(12) United States Patent
Harrison et al.

(10) Patent No.: US 11,673,141 B2
(45) Date of Patent: Jun. 13, 2023

(54) METHOD, APPARATUS, AND COMPUTER PROGRAM PRODUCT FOR CONTROLLING COMPONENTS OF A DETECTION DEVICE

(71) Applicant: bioMerieux, Inc., Durham, NC (US)

(72) Inventors: Joel Patrick Harrison, Maryville, IL (US); John Kenneth Korte, St. Louis, MO (US); Jeffrey Edward Price, Wildwood, MO (US)

(73) Assignee: BIOMERIEUX, INC., Durham, NC (US)

(*) Notice: Subject to any disclaimer, the term of this patent is extended or adjusted under 35 U.S.C. 154(b) by 10 days.

(21) Appl. No.: 17/474,544

(22) Filed: Sep. 14, 2021

(65) Prior Publication Data

US 2022/0097047 A1 Mar. 31, 2022

Related U.S. Application Data

(63) Continuation of application No. 15/958,722, filed on Apr. 20, 2018, now Pat. No. 11,148,144.

(Continued)

(51) Int. Cl.
*G01N 21/01* (2006.01)
*G01N 15/06* (2006.01)
(Continued)

(52) U.S. Cl.
CPC ............ *B01L 3/50853* (2013.01); *G01N 1/10* (2013.01); *G01N 15/06* (2013.01); *G01N 21/01* (2013.01);
(Continued)

(58) Field of Classification Search
None
See application file for complete search history.

(56) References Cited

U.S. PATENT DOCUMENTS

| 2,157,438 A | 5/1939 | Sparks |
| 2,436,262 A | 2/1948 | Miller |

(Continued)

FOREIGN PATENT DOCUMENTS

| CN | 3159492 | 1/2000 |
| CN | 3383938 | 11/2003 |

(Continued)

OTHER PUBLICATIONS

First Office Action and Search Report for Chinese Application No. 201880032807.X, 9 pgs., dated Feb. 8, 2022.

(Continued)

*Primary Examiner* — Brent A. Fairbanks
(74) *Attorney, Agent, or Firm* — Alston & Bird LLP

(57) ABSTRACT

A method, computer program product, and apparatus are provided for controlling components of a detection device. The device may detect turbidity of liquid with sensors such as a density sensor and/or nephelometric sensor. A light modulation pattern may reduce or eliminate interference in sensor readings. Readings may be performed during off cycles of an illumination light to reduce interference but to provide improved visibility of a tube. Dark and light sensor readings may be performed with an emitter respectively off or on to account for ambient light in subsequent readings. Readings from the density sensor and/or nephelometric sensor may be used to calculate McFarland values. The device may be zeroed based on an emitter level that results in a sensor reading satisfying a predetermined criterion.

20 Claims, 10 Drawing Sheets

Related U.S. Application Data

(60) Provisional application No. 62/488,450, filed on Apr. 21, 2017, provisional application No. 62/487,860, filed on Apr. 20, 2017, provisional application No. 62/487,736, filed on Apr. 20, 2017, provisional application No. 62/487,807, filed on Apr. 20, 2017, provisional application No. 62/487,796, filed on Apr. 20, 2017.

(51) Int. Cl.
| | |
|---|---|
| G01N 21/51 | (2006.01) |
| G01N 21/88 | (2006.01) |
| G01N 21/93 | (2006.01) |
| B01L 3/00 | (2006.01) |
| G01N 21/59 | (2006.01) |
| G01N 21/47 | (2006.01) |
| G01N 1/10 | (2006.01) |
| G01N 21/27 | (2006.01) |
| G01N 33/487 | (2006.01) |
| G01N 21/03 | (2006.01) |

(52) U.S. Cl.
CPC ....... *G01N 21/0303* (2013.01); *G01N 21/274* (2013.01); *G01N 21/4738* (2013.01); *G01N 21/4785* (2013.01); *G01N 21/51* (2013.01); *G01N 21/5907* (2013.01); *G01N 21/8806* (2013.01); *G01N 21/93* (2013.01); *G01N 33/487* (2013.01); *G01N 33/48735* (2013.01); *B01L 2200/14* (2013.01); *B01L 2300/0654* (2013.01); *B01L 2300/0803* (2013.01); *B01L 2300/12* (2013.01); *G01N 21/474* (2013.01); *G01N 2015/0693* (2013.01); *G01N 2021/0168* (2013.01); *G01N 2021/0389* (2013.01); *G01N 2021/4769* (2013.01); *G01N 2021/598* (2013.01); *G01N 2201/126* (2013.01); *G01N 2201/12707* (2013.01)

(56) References Cited

U.S. PATENT DOCUMENTS

| | | | |
|---|---|---|---|
| 2,863,354 A | 12/1958 | Diehl et al. | |
| 2,874,606 A | 2/1959 | Leiterer | |
| 3,554,648 A | 1/1971 | Boostrom et al. | |
| 3,712,144 A | 1/1973 | Kuzel et al. | |
| 3,714,445 A | 1/1973 | Blachere et al. | |
| 3,775,013 A | 11/1973 | Simms | |
| 3,783,635 A | 1/1974 | Perez | |
| 3,809,912 A | 5/1974 | Henning | |
| 3,826,574 A | 7/1974 | Brown, Jr. | |
| 3,962,041 A | 6/1976 | Muller et al. | |
| 3,977,794 A | 8/1976 | Liedholz | |
| 4,118,625 A | 10/1978 | Underwood | |
| 4,136,953 A * | 1/1979 | Klein | G01N 21/51 356/246 |
| 4,193,692 A | 3/1980 | Wynn | |
| 4,291,983 A | 9/1981 | Kraft et al. | |
| 4,343,552 A | 8/1982 | Blades | |
| 5,137,693 A | 8/1992 | Mawhirt | |
| 5,140,168 A | 8/1992 | King | |
| 5,331,177 A | 7/1994 | Kunisiak et al. | |
| 5,506,679 A | 4/1996 | Cooper et al. | |
| 5,604,590 A | 2/1997 | Cooper et al. | |
| 5,616,923 A | 4/1997 | Rich et al. | |
| 5,651,941 A | 7/1997 | Stark et al. | |
| 5,687,849 A | 11/1997 | Borenstein et al. | |
| 5,736,410 A * | 4/1998 | Zarling | B82Y 15/00 436/63 |
| 5,863,754 A | 1/1999 | Bajard | |
| 5,867,266 A | 2/1999 | Craighead | |
| 5,872,361 A | 2/1999 | Paoli et al. | |
| 5,940,178 A * | 8/1999 | Barber | G01N 35/025 422/534 |
| D439,673 S | 3/2001 | Brophy et al. | |
| 6,198,536 B1 | 3/2001 | Baker | |
| 6,274,092 B1 | 8/2001 | Itoh | |
| D453,573 S | 2/2002 | Lafond et al. | |
| 6,359,689 B1 | 3/2002 | Stansell et al. | |
| 6,537,772 B1 | 3/2003 | Alarcon et al. | |
| 7,485,264 B2 | 2/2009 | Itoh | |
| 7,659,980 B1 | 2/2010 | Mitchell et al. | |
| D624,194 S | 9/2010 | Pack et al. | |
| 7,910,067 B2 | 3/2011 | Knight et al. | |
| 8,147,777 B2 | 4/2012 | Schacher et al. | |
| D679,412 S | 4/2013 | Khamu | |
| D687,567 S | 8/2013 | Jungheim et al. | |
| D709,625 S | 7/2014 | Baum et al. | |
| 9,612,196 B2 | 4/2017 | Saraswat et al. | |
| 10,591,416 B2 | 3/2020 | Chen et al. | |
| 2003/0005928 A1 | 1/2003 | Appel et al. | |
| 2003/0058450 A1* | 3/2003 | Mosley | G01N 21/643 356/436 |
| 2003/0085221 A1* | 5/2003 | Smolenski | H05B 1/0208 219/501 |
| 2003/0139886 A1* | 7/2003 | Bodzin | G01N 21/47 702/28 |
| 2004/0147843 A1 | 7/2004 | Bambot et al. | |
| 2005/0106746 A1* | 5/2005 | Shinn | G01N 21/532 436/164 |
| 2006/0001865 A1 | 1/2006 | Bellalou et al. | |
| 2007/0269853 A1 | 11/2007 | Galiano | |
| 2008/0072664 A1 | 3/2008 | Hansen et al. | |
| 2008/0079943 A1 | 4/2008 | Li | |
| 2010/0028859 A1 | 2/2010 | Moshe et al. | |
| 2010/0110220 A1* | 5/2010 | Leugers | G01N 21/59 348/E5.022 |
| 2010/0245827 A1* | 9/2010 | Palumbo | G01N 21/13 356/440 |
| 2011/0151503 A1 | 6/2011 | Galiano | |
| 2011/0270128 A1 | 11/2011 | Zhao et al. | |
| 2011/0306032 A1 | 12/2011 | Galiano et al. | |
| 2011/0306087 A1 | 12/2011 | Galiano et al. | |
| 2011/0307183 A1* | 12/2011 | Galiano | G01N 21/61 702/19 |
| 2012/0009558 A1 | 1/2012 | Armstrong et al. | |
| 2012/0022794 A1* | 1/2012 | Andelic | G01N 21/49 702/23 |
| 2012/0063956 A1 | 3/2012 | Truex et al. | |
| 2012/0082446 A1* | 4/2012 | Kumai | A61B 1/0669 396/164 |
| 2012/0140230 A1 | 6/2012 | Miller | |
| 2013/0022962 A1 | 1/2013 | Galiano | |
| 2013/0258336 A1 | 10/2013 | Ostermeyer et al. | |
| 2014/0233015 A1 | 8/2014 | Mander | |
| 2015/0031051 A1* | 1/2015 | Mohan | G01N 21/645 359/383 |
| 2015/0036121 A1* | 2/2015 | Kurowski | G01N 15/06 356/338 |
| 2015/0086971 A1 | 3/2015 | Botma et al. | |
| 2015/0108076 A1 | 4/2015 | Branch et al. | |
| 2015/0355208 A1 | 12/2015 | German | |
| 2016/0160260 A1 | 6/2016 | Marshall et al. | |
| 2016/0209328 A1* | 7/2016 | Berndt | G01N 15/06 |
| 2016/0266028 A1 | 9/2016 | Wyatt | |
| 2016/0341945 A1* | 11/2016 | Ou | H04N 23/56 |
| 2017/0307525 A1 | 10/2017 | Langoff et al. | |
| 2019/0129156 A1* | 5/2019 | Knebel | G02B 21/367 |
| 2019/0162744 A1* | 5/2019 | Kazama | G01N 21/51 |

FOREIGN PATENT DOCUMENTS

| | | |
|---|---|---|
| CN | 2919238 | 7/2007 |
| CN | 300905477 D | 12/2007 |
| CN | 201141824 | 10/2008 |
| CN | 301068253 | 11/2008 |
| CN | 204142554 | 2/2010 |
| CN | 101893564 A | 11/2010 |
| CN | 102128814 A | 7/2011 |
| CN | 103645162 A | 3/2014 |

(56) References Cited

FOREIGN PATENT DOCUMENTS

| | | |
|---|---|---|
| CN | 203479704 | 3/2014 |
| CN | 302968146 S | 6/2014 |
| CN | 302983583 S | 6/2014 |
| CN | 302995249 S | 6/2014 |
| CN | 103923827 | 7/2014 |
| CN | 303227067 S | 12/2014 |
| CN | 104266895 | 1/2015 |
| CN | 105277472 A | 1/2016 |
| CN | 105492890 A | 4/2016 |
| CN | 105593665 A | 5/2016 |
| CN | 205246536 U | 5/2016 |
| DE | 3516529 | 11/1986 |
| DE | 3608552 A1 | 9/1987 |
| DE | 202004020585 | 9/2005 |
| EP | 3023768 | 5/2016 |
| GB | 150 183 A | 9/1920 |
| GB | 4028381 | 1/2013 |
| GB | 4028382 | 1/2013 |
| JP | 3049676 | 6/1998 |
| JP | H10 284848 A | 10/1998 |
| JP | 3061144 | 9/1999 |
| JP | 2003/000224 | 1/2003 |
| KR | 100580312 | 5/2006 |
| KR | 20090081998 | 7/2009 |
| KR | 20090082060 | 7/2009 |
| KR | 100580313 | 5/2018 |
| TW | 201215873 A | 4/2012 |
| WO | WO 1993/009440 A1 | 5/1993 |
| WO | WO 1995/25950 A1 | 9/1995 |
| WO | WO 1998/000701 A1 | 1/1998 |
| WO | WO 1998/047999 A1 | 10/1998 |
| WO | WO 2000/065332 A1 | 11/2000 |
| WO | WO 2001/063253 A1 | 8/2001 |
| WO | WO 2004/015136 A1 | 2/2004 |
| WO | WO 2008/039442 A1 | 4/2008 |
| WO | WO 2010/090391 A2 | 8/2010 |
| WO | WO 2010/097687 A1 | 9/2010 |
| WO | WO 2010/108804 A1 | 9/2010 |
| WO | WO 2014/137333 A1 | 9/2014 |
| WO | WO 2015/026794 A1 | 2/2015 |
| WO | WO 2015/164274 A1 | 10/2015 |
| WO | WO 2016/049604 A1 | 3/2016 |
| WO | WO 2016/051267 A1 | 4/2016 |
| WO | WO 2016/191646 A1 | 12/2016 |
| WO | WO 2018/195509 A1 | 10/2018 |

OTHER PUBLICATIONS

Office Action for European Application No. 18724031.2 dated Oct. 7, 2021.
International Search Report and Written Opinion for Application No. PCT/US2018/028699 dated Jul. 16, 2018, 14 pages.
International Search Report and Written Opinion for Application No. PCT/US2018/028696 dated Sep. 7, 2018.
International Search Report and Written Opinion for Application No. PCT/US2018/028701 dated Sep. 10, 2018.
International Search Report and Written Opinion for Application No. PCT/US2018/028702 dated Sep. 10, 2018.
Office Action for European Application No. 18724032.0 dated Jan. 28, 2021.
Office Action for Australian Patent Application No. 2018254602 dated Jan. 27, 2021.
Office Action for Canadian Patent Application No. 3,061,024 dated May 27, 2021.
Office Action for Indian Patent Application No. 201917045483 dated Feb. 17, 2021.
Office Action for Canadian Patent Application No. 3,061,074 dated May 13, 2021.
Office Action for Canadian Patent Application No. 3,060,377 dated May 28, 2021.
Office Action for Chinese Application No. 2018800328421 dated Nov. 18, 2021.
Non-Final Office Action for U.S. Appl. No. 17/524,044, 15 pgs., dated Jan. 12, 2023.
Non-Final Office Action for U.S. Appl. No. 17/470,717, 11 pgs., dated Feb. 2, 2023.

* cited by examiner

METHOD, APPARATUS, AND COMPUTER PROGRAM PRODUCT FOR CONTROLLING COMPONENTS OF A DETECTION DEVICE

CROSS-REFERENCE TO RELATED APPLICATIONS

This application is a continuation of U.S. patent application Ser. No. 15/958,722 filed Apr. 20, 2018 which claims the benefit of each of the following: U.S. Provisional Application No. 62/487,736, which is entitled "Method, Apparatus, And Computer Program Product For Controlling Components Of A Detection Device" and was filed Apr. 20, 2017; U.S. Provisional Application No. 62/487,796, which is entitled "Optical Density Instrument And Systems And Methods Using The Same" and was filed Apr. 20, 2017; U.S. Provisional Application No. 62/488,450, which is entitled "Optical Density Instrument And Systems And Methods Using The Same" and was filed Apr. 21, 2017; U.S. Provisional Application No. 62/487,860, which is entitled "Tip Resistant Optical Testing Instrument" and was filed Apr. 20, 2017; and U.S. Provisional Application No. 62/487,807, which is entitled "Optical Test Platform" and was filed Apr. 20, 2017. Each of the foregoing applications is hereby incorporated by reference in its entirety.

TECHNOLOGICAL FIELD

Embodiments of the present invention relate generally to computer technology for controlling components of a detection device. More particularly, embodiments relate to methods, apparatuses, and computer program products for modulating an illumination light, determining McFarland values from a density sensor and nephelometric sensor, and zeroing a detection device.

BACKGROUND

In microbiology laboratories and other similar settings, lab technicians, scientists, and other practitioners use laboratory equipment to measure conditions of liquid suspensions. The suspensions may be observed and manipulated in clear polystyrene test tubes, glass test tubes, or other similar vials. The practitioner may utilize various devices or instruments to perform readings and measurements on the liquid in a tube. The practitioner may also manipulate the fluid while performing measurements, or intermittingly between measurements. In some examples, a practitioner may manipulate the fluid while monitoring a measurement or reading performed by an instrument.

One example of such a measurement performed in a microbiology lab includes measuring the turbidity and/or concentration of microorganisms in the liquid. One readout for this measurement of turbidity and/or concentration of microorganisms in the liquid that can be obtained is known as a McFarland value. A McFarland value is obtained using a series of McFarland standards, which are a series of known concentrations of solutions that are used to prepare a standard curve in order to determine the concentration of particles in an unknown sample. While working with the tubes, the practitioner may dilute the solutions with saline, or increase the levels of microorganisms in the fluid. Sensors in a device or instrument may be configured to detect light emitted in the area of the tube to measure characteristics of the liquid, such as but not limited to McFarland values.

BRIEF SUMMARY

Methods, apparatuses, and computer program products are therefore provided for controlling components of a detection device.

In some embodiments, an illumination light may be included in the detection device to improve visibility of a tube and its contents. However, the illumination light may interfere with sensors that perform readings such as those dependent on sensitive optics and/or detection of emitted light. Example embodiments may modulate the illumination light such that sensor readings are performed during an off cycle of the illumination light. The illumination light may therefore still provide improved visibility for the user and the interference may be reduced or prevented.

Some embodiments may include or communicate with a density sensor and/or nephelometric sensor. As described herein, readings from the density sensor and/or nephelometric sensor may be used to calculate McFarland values. In some embodiments, the detection device may be zeroed based on an emitter level that results in a sensor reading satisfying a predetermined criterion.

A method is provided for reducing light interference in sensor readings. The method includes causing an illumination light to be powered on and off according to a light modulation pattern, and, during an off cycle of the light modulation pattern, controlling at least one emitter to emit a signal for detection by at least one sensor. The method further includes controlling the at least one sensor to perform a reading during the off cycle of the light modulation pattern. The method may further include controlling the at least one sensor to perform a dark reading while the at least one emitter is off, determining an ambient light offset by subtracting the dark reading from a light reading, and calibrating sensor readings according to the ambient light offset.

The method may further include controlling the at least one sensor to perform a plurality of readings over a plurality of off cycles in the light modulation pattern, and calculating a moving average sensor reading based on the plurality of readings. The method may further include controlling sensor readings to begin after a predetermined delay after a start of a respective off cycle of the light modulation pattern. In some embodiments, the method includes receiving an indication of a tube insertion, and controlling sensor reading cycles to begin after a predetermined initial delay after the receipt of the indication of the tube insertion.

A method is provided for determining a McFarland value. The method includes receiving a plurality of density sensor readings, receiving a plurality of nephelometric sensor readings, and applying linear regression to the density sensor readings and the nephelometric sensor readings to determine coefficients of a polynomial equation, and applying subsequent readings to the polynomial equation to calculate the McFarland value. The method may further include detecting an error in at least one sensor based on a comparison of the density sensor readings and the nephelometric sensor readings.

A method for zeroing a detection device is provided. The method includes receiving an indication to perform a zeroing calibration, and in response to the indication of the zeroing calibration, controlling an emitter to step up an emitted signal. The method further includes controlling at least one sensor to perform readings based on the emitted signal, monitoring the sensor reading and storing a level of the emitted signal when the sensor reading satisfies a predetermined criterion, and controlling the emitter to operate based on the stored level of the emitted signal.

A computer program product is provided for reducing light interference in sensor readings. The computer program product comprises at least one non-transitory computer-readable medium having computer-readable program instructions stored therein, the computer-readable program instructions comprising instructions, which when performed by an apparatus, are configured to cause the apparatus to cause an illumination light to be powered on and off according to a light modulation pattern. The computer-readable program instructions may further comprise instructions to, during an off cycle of the light modulation pattern, control at least one emitter to emit a signal for detection by at least one sensor, and control the at least one sensor to perform a reading during the off cycle of the light modulation pattern.

A computer program product is also provided for determining a McFarland value. The computer program product includes at least one non-transitory computer-readable medium having computer-readable program instructions stored therein, the computer-readable program instructions comprising instructions, which when performed by an apparatus, are configured to cause the apparatus to receive a plurality of density sensor readings, receive a plurality of nephelometric sensor readings, apply linear regression to the density sensor readings and the nephelometric sensor readings to determine coefficients of a polynomial equation, and apply subsequent readings to the polynomial equation to calculate the McFarland value.

A computer program product is provided for zeroing a detection device, wherein the computer-readable program instructions further comprise instructions, which when performed by an apparatus, are configured to cause the apparatus to at least receive an indication to perform a zeroing calibration, in response to the indication of the zeroing calibration, control an emitter to step up an emitted signal, control at least one sensor to perform readings based on the emitted signal, monitor the sensor reading and store a level of the emitted signal when the sensor reading satisfies a predetermined criterion, and control the emitter to operate based on the stored level of the emitted signal.

An apparatus is provided for reducing light interference in sensor readings, the apparatus comprising processing circuitry configured to cause the apparatus to cause an illumination light to be powered on and off according to a light modulation pattern, during an off cycle of the light modulation pattern, control at least one emitter to emit a signal for detection by at least one sensor, and control the at least one sensor to perform a reading during the off cycle of the light modulation pattern.

An apparatus for determining a McFarland value is provided, the apparatus comprising processing circuitry configured to cause the apparatus to receive a plurality of density sensor readings, receive a plurality of nephelometric sensor readings, apply linear regression to the density sensor readings and the nephelometric sensor readings to determine coefficients of a polynomial equation, and apply subsequent readings to the polynomial equation to calculate the McFarland value.

An apparatus is provided for zeroing a detection device, the apparatus comprising processing circuitry configured to cause the apparatus to receive an indication to perform a zeroing calibration, in response to the indication of the zeroing calibration, control an emitter to step up an emitted signal, control at least one sensor to perform readings based on the emitted signal, monitor the sensor reading and store a level of the emitted signal when the sensor reading satisfies a predetermined criterion, and control the emitter to operate based on the stored level of the emitted signal.

An apparatus is provided with means for reducing light interference in sensor readings. The apparatus includes means for causing an illumination light to be powered on and off according to a light modulation pattern. The apparatus includes means for, during an off cycle of the light modulation pattern, controlling at least one emitter to emit a signal for detection by at least one sensor. The apparatus further includes means for controlling the at least one sensor to perform a reading during the off cycle of the light modulation pattern.

An apparatus is provided for determining a McFarland value. The apparatus includes means for receiving a plurality of density sensor readings, means for receiving a plurality of nephelometric sensor readings, and means for applying linear regression to the density sensor readings and the nephelometric sensor readings to determine coefficients of a polynomial equation. The apparatus further includes means for applying subsequent readings to the polynomial equation to calculate the McFarland value.

An apparatus is provided for zeroing a detection device. The apparatus includes means for receiving an indication to perform a zeroing calibration, and in response to the indication of the zeroing calibration, means for controlling an emitter to step up an emitted signal. The apparatus further includes means for controlling at least one sensor to perform readings based on the emitted signal, means for monitoring the sensor reading and means for storing a level of the emitted signal when the sensor reading satisfies a predetermined criterion. The apparatus further includes means for controlling the emitter to operate based on the stored level of the emitted signal.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
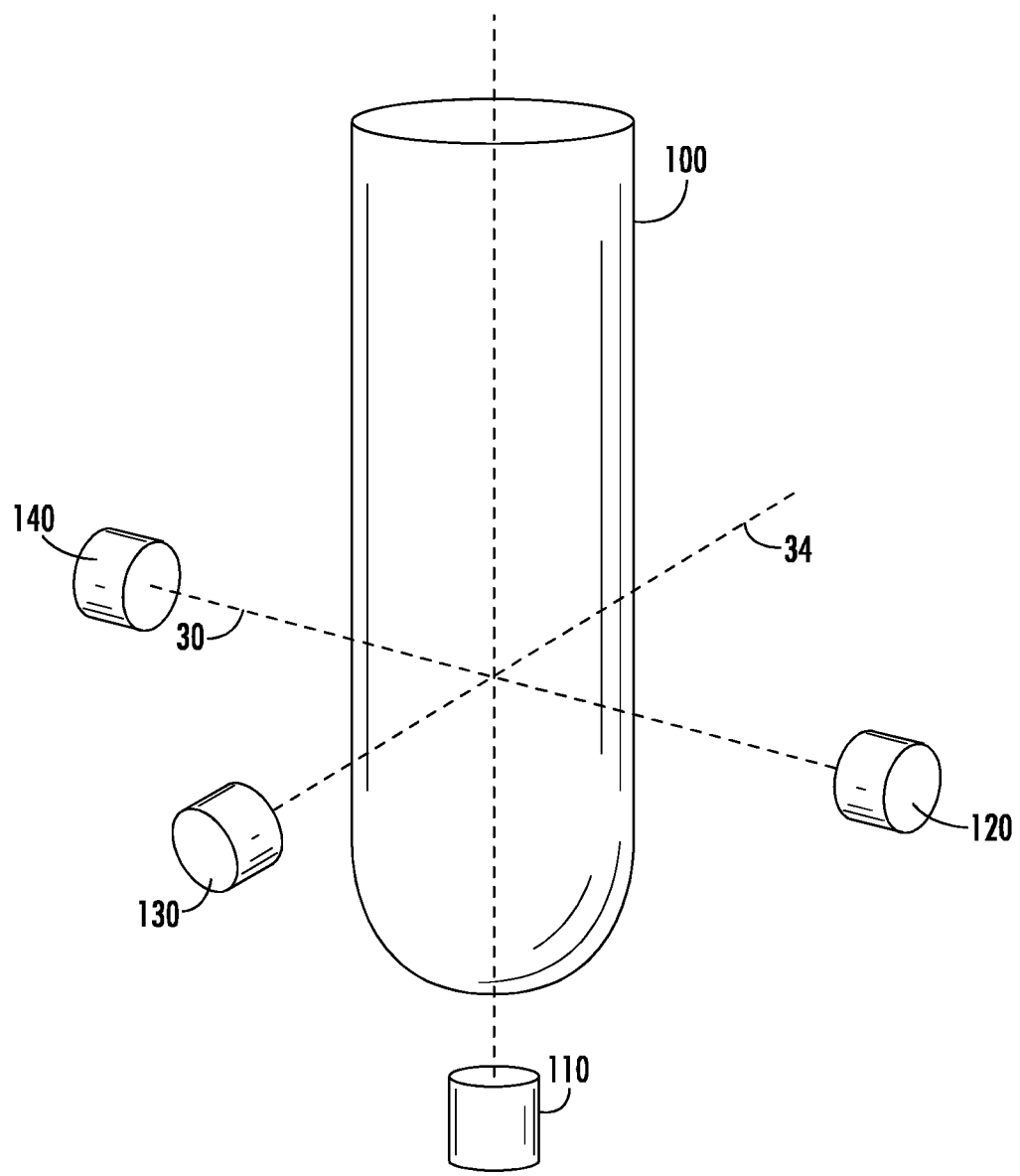
Figure 2:
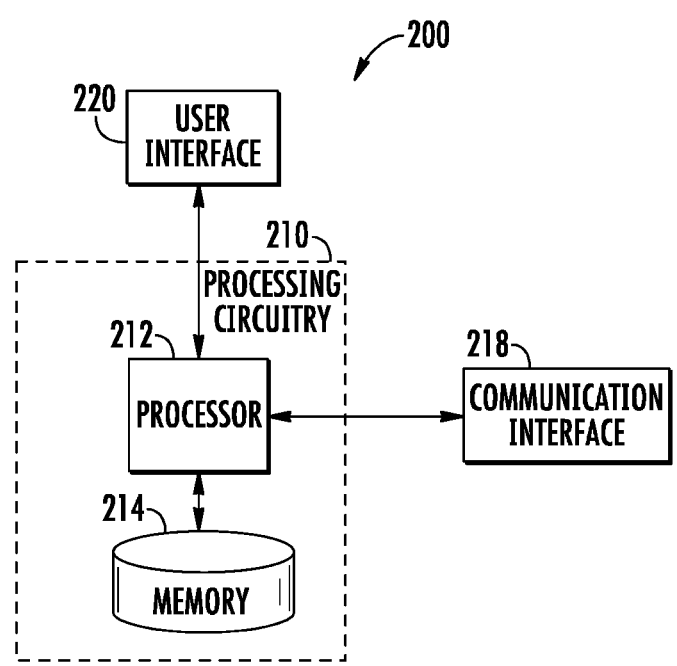
Figure 3:
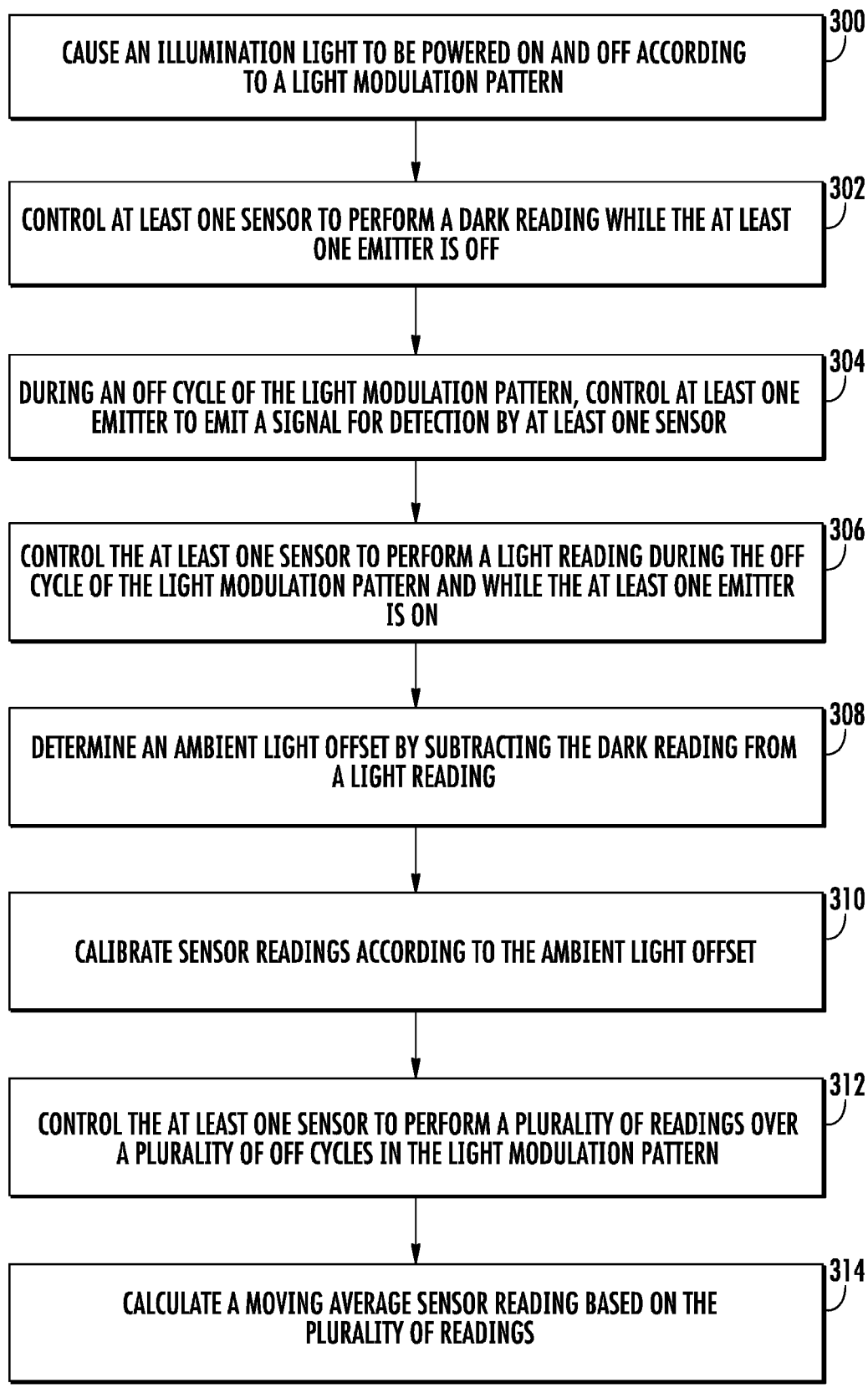
Figure 4:
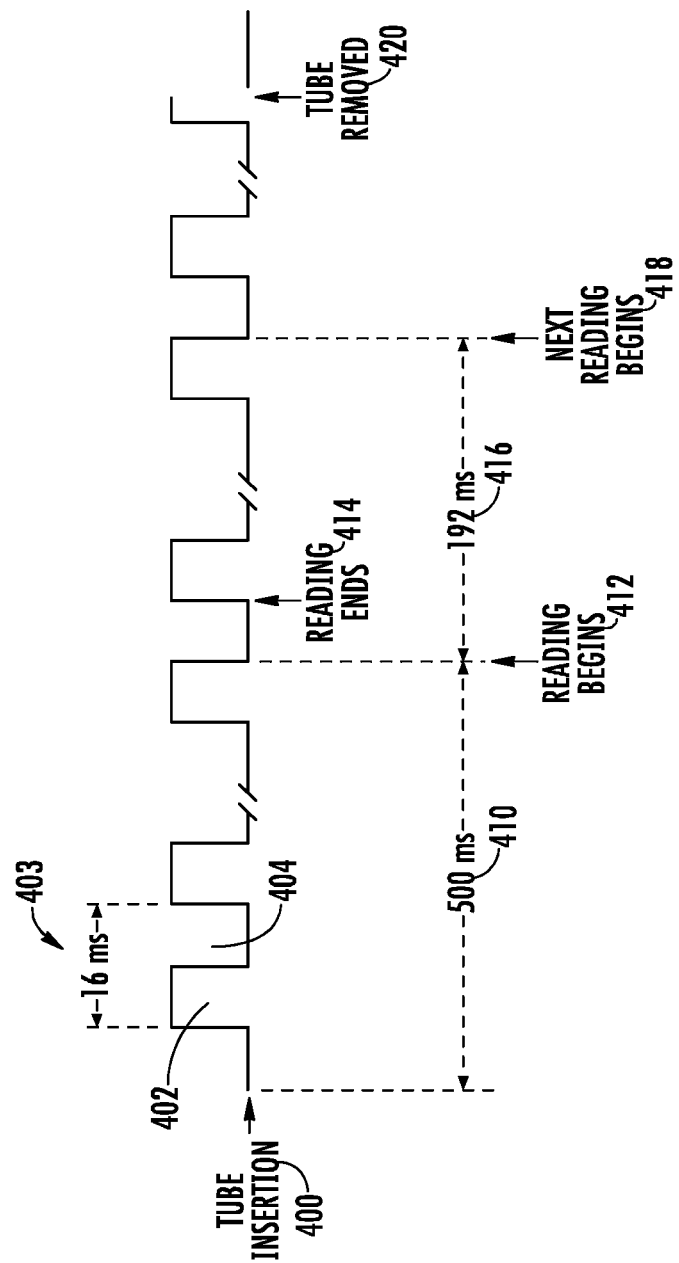
Figure 5:
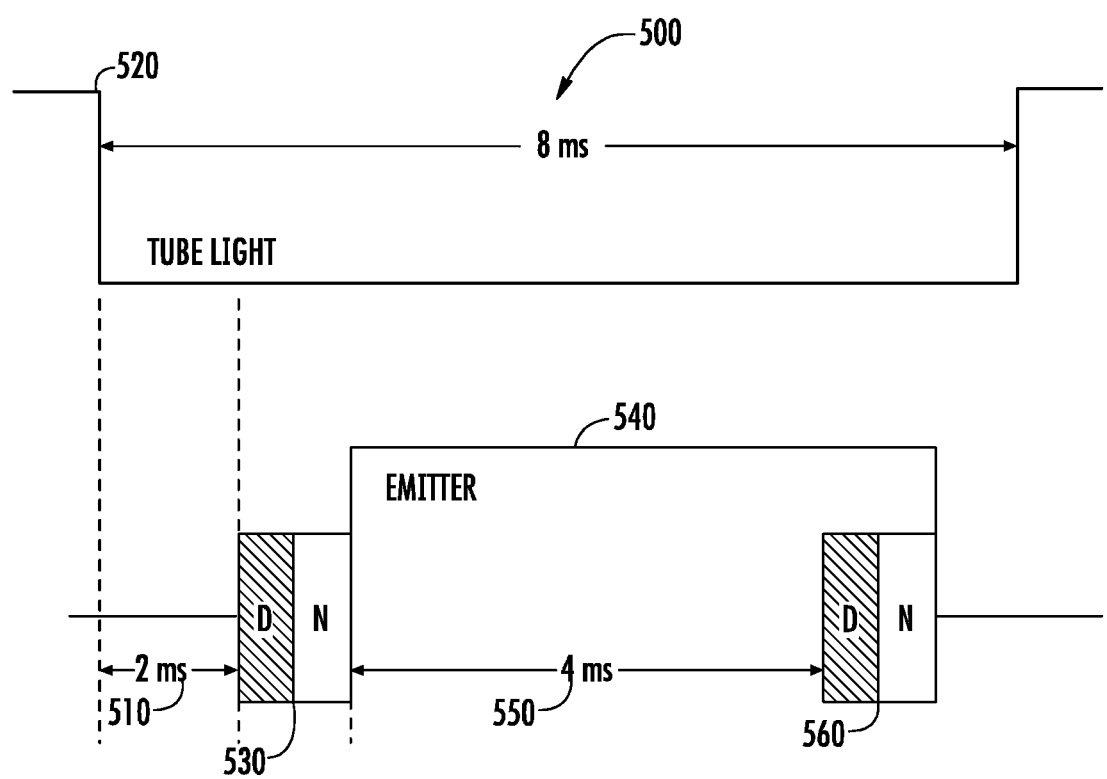
Figure 6:
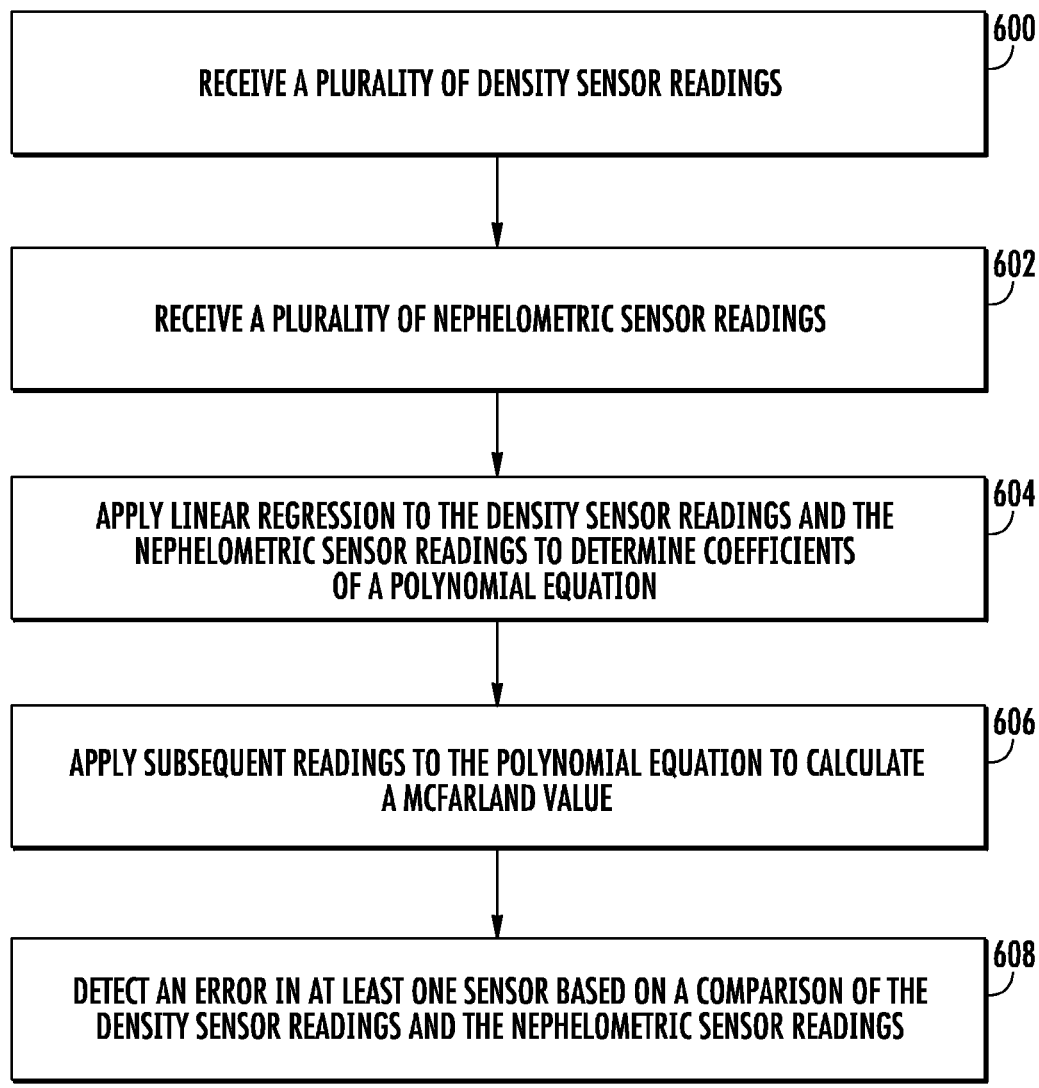
Figure 7:
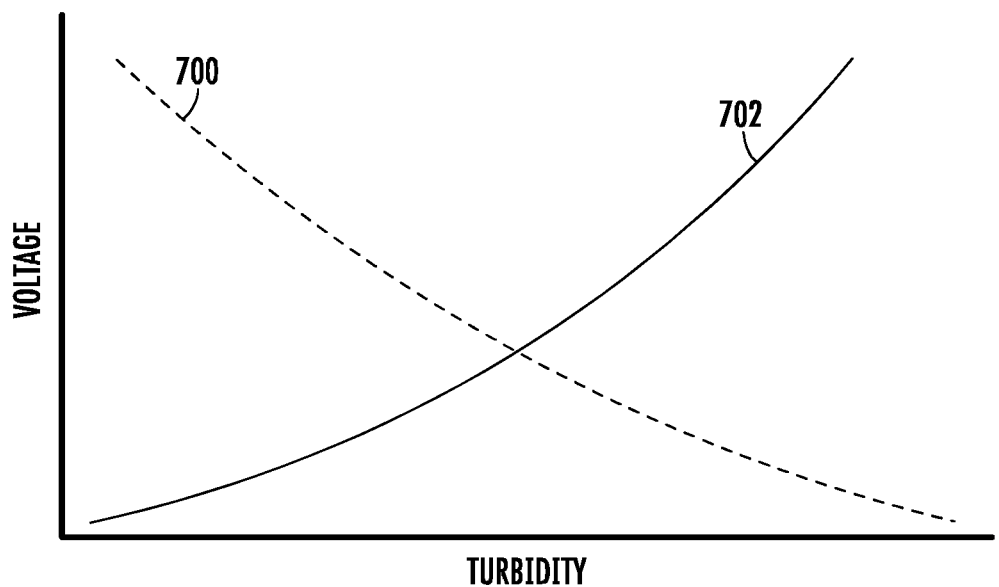
Figure 8:
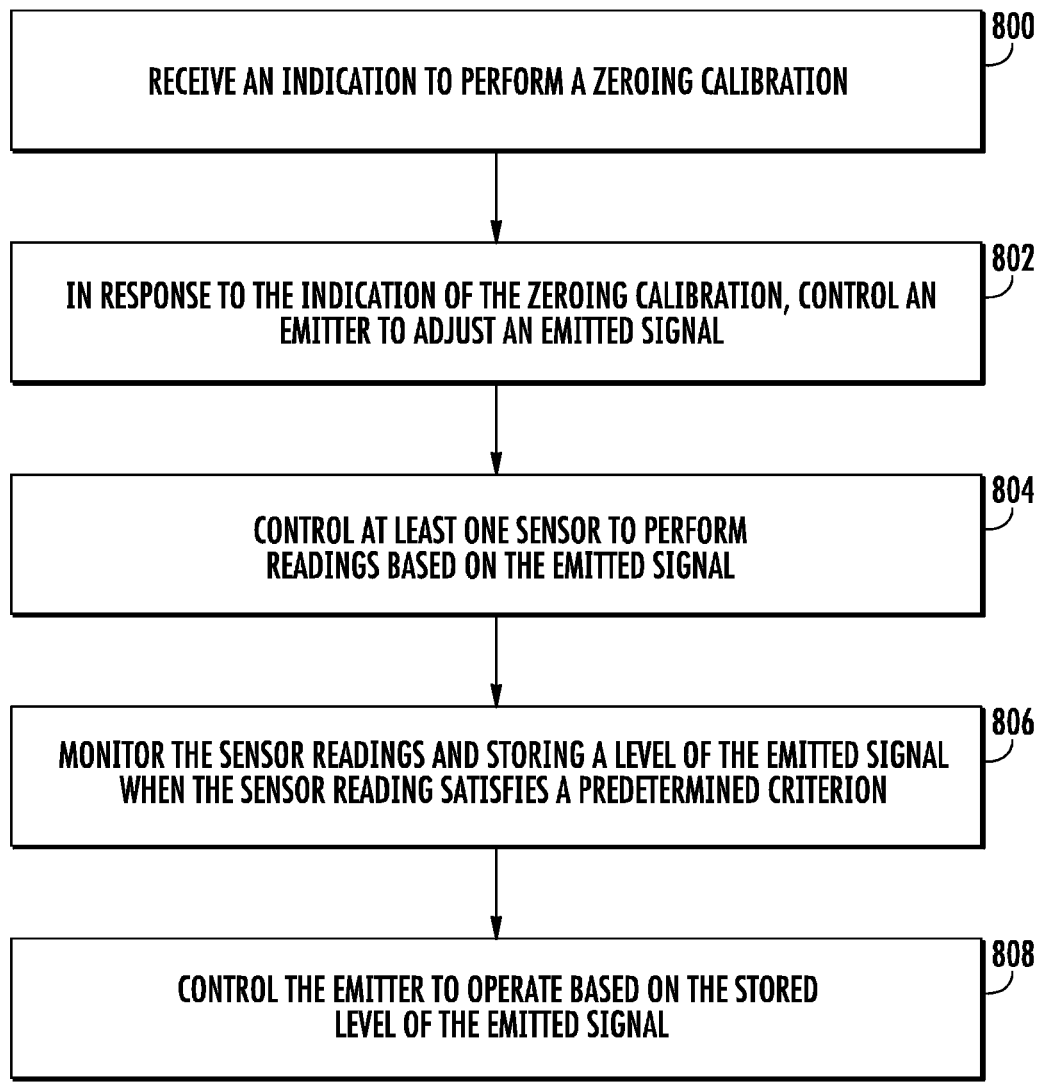
Figure 9:
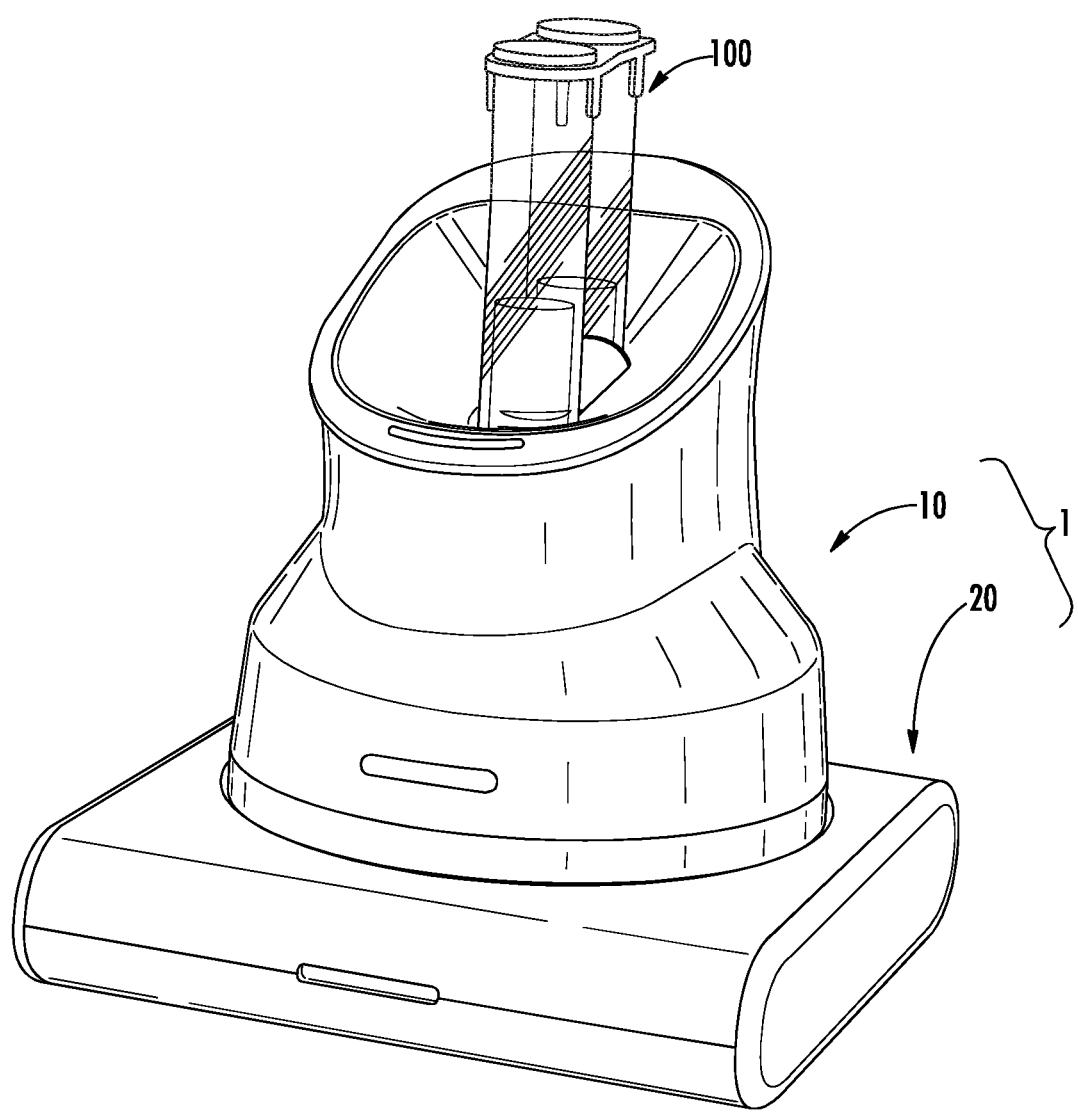
Figure 10:
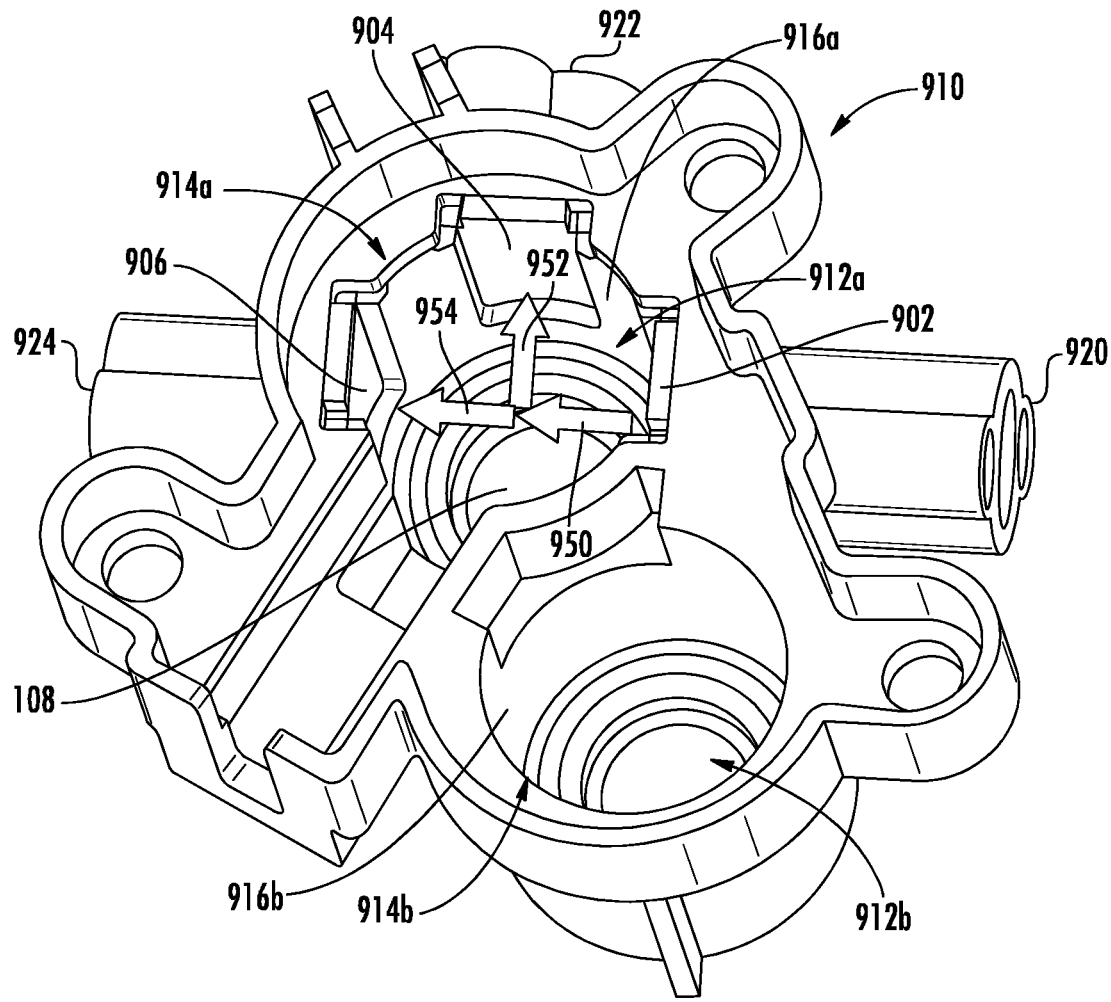

Having thus described embodiments of the invention in general terms, reference will now be made to the accompanying drawings, which are not necessarily drawn to scale, and wherein:

FIG. 1 is an example schematic of detection device components according to some example embodiments;

FIG. 2 is a block diagram of an apparatus according to some example embodiments;

FIG. 3 is a flowchart illustrating operations according to some example embodiments;

FIGS. 4 and 5 are example timing diagrams according to some example embodiments;

FIG. 6 is a flowchart illustrating operations according to some example embodiments;

FIG. 7 is an example plot of sensor readings according to some example embodiments;

FIG. 8 is a flowchart illustrating operations according to some example embodiments;

FIG. 9 is a perspective view of a detection instrument according to some example embodiments; and FIG. 10 shows optical paths of light traveling through a shell of the detection instrument according to some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

Overview

FIG. 1 is an example schematic of detection device components according to some example embodiments. FIG. 1 is provided merely as an example and it will be appreciated that many other configurations of detection devices may be employed according to example embodiments.

As illustrated in FIG. 1, in some embodiments, a tube 100 may be inserted into a detection device housing (not shown). The detection device may comprise an illumination light 110 (e.g., illuminator or tube light), configured to illuminate a tube 100. Although one tube 100 is present in FIG. 1 and referred to herein, it will be appreciated that any number of tubes 100 may be inserted into the detection device and may be subject to the operations described herein according to example embodiments.

The illumination light 110 may be any type of light configured to illuminate a tube 100. The illumination light 110 may illuminate the tube, or emit light upwardly into the tube, such that a practitioner or user of the detection device can more clearly see or observe the contents of the clear tube relative to operating the detection device without an illumination light, or relative to operating the detection device with external light sources only. The illumination light 110 may be any type of lighting device, such as a light-emitting diode (LED). As illustrated in FIG. 1, the illumination light 110 may be configured in the device such that when a tube is inserted, the illumination light 100 is positioned underneath an inserted tube such that the tube can be illuminated. In other example embodiments, the illumination light 110 may be positioned in any other position relative to components of the detection device such light is provided in the area of an inserted tube and helps a user of the device to see the tube contents.

The detection device may include at least one emitter 140 (e.g., an LED or other light source) for emitting light into the sample tube 100 and at least one detector or sensor 120, 130 (e.g., a photodetector) for receiving light that passes through the sample. For example, in the illustrated embodiment of FIG. 1, one emitter 140 and two sensors 120 and 130 may be used to generate an optical density reading of a sample. In operation, the emitter 140 may transmit light into the sample and a portion of the transmitted light passes through the sample to a first sensor 120 positioned opposite the emitter 140 relative to the tube 100, while a second portion of the transmitted light reflects off of the sample and is collected by a second sensor 130 perpendicular to the transmission direction of the emitter. In particular, the first sensor 120 may be oriented collinearly relative to the axis 30 of the emitter 140 and may be oriented 180 degrees offset from the emitter 140 with respect to the axis 32 of the sample tube 100. The second sensor 130 may be positioned 90 degrees about the radial circumference of the sample tube 100 from both the emitter 140 and first sensor 120 on an orthogonal axis 34 to collect reflected light. The emitter 140 may be configured to transmit the light perpendicular to the surface of the tube 100 and perpendicular to the longitudinal axis 32 of the sample tube 100.

The portion of light collected by the first, pass-through sensor 120 may be called the "density" reading, and the portion of light collected by the second, reflective sensor 130 may be called the "nephelometric" reading. In this regard, sensor 120 may be referred to as a density sensor 120, and sensor 130 may be referred to as a nephelometric sensor 130. The detection device may combine the density and nephelometric signals from each sensor 120 and 130 to generate a McFarland reading (or other optical measurement) of the sample.

The emitter 140 may therefore be any type of device configured to emit a signal for detection by a sensor. The signal emitted by emitter 140 may include but is not limited to infrared (IR) wavelengths, near-infrared (NIR) wavelengths, electromagnetic radiation, and/or other types of light (including visible and/or non-visible light). For example, in some embodiments, the emitter 140 may be an LED, infrared LED and/or the like. For simplicity, the signal emitted by emitter 140 may be referred to herein as a source light, but it will be appreciated that any of the aforementioned signal types may be employed.

In some embodiments, the density sensor 120 (which may be considered an optical density sensor) may be configured to measure a mass of microorganisms or other matter in a liquid suspension based on an amount of source light that passes through the tube and is detected by the density sensor 120. In this regard, the density sensor 120 may be positioned in the detection device such that when a tube is inserted, the emitter 140 is positioned on the opposite side of the tube from the density sensor 120 such that the source light passes through the tube and is detected by the density sensor 120.

In some embodiments, the nephelometric sensor 130 may be configured to measure a concentration of suspended particles in the liquid suspension. The nephelometric sensor 130 may be configured in the detection device such that it is perpendicular or substantially perpendicular to the emitter 140. The source light may reflect off of suspended particles in the liquid and the scattered source light may be detected by the nephelometric sensor 130 to measure the turbidity or concentration.

Density sensor 120 and nephelometric sensor 130 are provided merely as example sensors, and may be optional in some embodiments. It will be appreciated that a variety of other types of sensors and/or receivers may be present and may be employed according to example embodiments. For example, the density sensor 120 and nephelometric sensor 130 may be any type of photodetector or other optical sensor, including, but not limited to, charge-coupled devices (CCD); active-pixel sensors (APSs) such as complementary metal-oxide-semiconductor (CMOS) sensors; reverse-biased LEDs, photodiodes, phototransistors, photoresistors, photomultipliers, or any other sensor capable of determining an intensity of incident light at the sensor. In some embodiments, a sensor of the detection device may comprise an analog-to-digital converter configured to convert a detected voltage to a standardized reading.

FIG. 2 illustrates an example apparatus 200 that may embody or at least partially embody the detection device, or may be commutatively connected to the detection device or any components thereof. For example, the sensor(s) of the detection device, such as density sensor 120 and/or nephelometric sensor 130 may be configured to communicate with processing circuitry 210 (including processor 212 and/or memory 214) via a communication interface 218. However, it should be noted that the components, devices, and elements illustrated in and described with respect to FIG. 2 below may not be mandatory and thus some may be omitted in certain embodiments. For example, FIG. 2 illustrates a user interface 220, as described in more detail below, which may be optional in some embodiments. Additionally, some embodiments may include further or different components, devices, or elements beyond those illustrated in and described with respect to FIG. 2.

In some embodiments, apparatus 200 may be implemented as or at least partially as a distributed system or cloud based system and may therefore include any number of remote user devices and/or server devices. Accordingly, example embodiments may not necessarily be limited to use in a laboratory settings, but may be implemented, for example in a manufacturing setting or other environment such that remote processing and/or monitoring of data collected by the detection device may be performed on servers and/or other like computing devices. Regardless of implementation, apparatus 200 may be configured to control various components of the detection device as described herein.

Continuing with FIG. 2, processing circuitry 210 may be configured to perform actions in accordance with one or more example embodiments disclosed herein. In this regard, the processing circuitry 210 may be configured to perform and/or control performance of one or more functionalities of the detection device and/or components thereof in accordance with various example embodiments. For example, the processing circuitry 210 may be in communication with or otherwise control communication interface 218, user interface 220, illumination light 110, density sensor 120, nephelometric sensor 130, emitter 140, and/or other components of the apparatus 200 such as other sensors. For example, the processing circuitry may control the illumination light 110 to be powered on and off, the emitter 140 to emit a signal, and any of the sensors to perform a reading. The processing circuitry 210 may be further configured to perform data processing, such as processing of data collected by a sensor, and/or other processing and management services according to one or more example embodiments. In some embodiments, apparatus 200, or a component(s) thereof, such as the processing circuitry 210, may be embodied as or comprise a circuit chip (e.g., an integrated circuit chip) configured (e.g., with hardware, software, or a combination of hardware and software) to perform operations described herein. The circuit chip may constitute means for performing one or more operations for providing the functionalities described herein. In some example embodiments, the processing circuitry 210 may include a processor 212, and in some embodiments, such as that illustrated in FIG. 2, may further include memory 214.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of the apparatus 200 and/or detection device as described herein. The plurality of processors may be embodied on a single computing device or distributed across a plurality of computing devices collectively configured to function as apparatus 200. For example, some operations performed herein may be performed by components of the detection device while some operations may be performed on a remote device communicatively connected to the detection device. For example, a user device such as a smart phone, tablet, personal computer and/or the like may be configured to communicate with the detection device such as by Bluetooth™ communication or over a local area network. Additionally or alternatively, a remote server device may perform some of the operations described herein, such as processing data collected by any of the sensors, and providing or communicating resultant data to other devices accordingly.

In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments.

The memory 214 may be configured to buffer input data for processing by the processor 212. Additionally or alternatively, the memory 214 may be configured to store instructions for execution by the processor 212. In some embodiments, the memory 214 may include one or more databases that may store a variety of files, contents, or data sets. Among the contents of the memory 214, applications may be stored for execution by the processor 212 to carry out the functionality associated with each respective application. For example, memory 214 may store data detected by a sensor(s) of the detection device, and/or application code for processing such data according to example embodiments. In some cases, the memory 214 may be in communication with one or more of the processor 212, communication interface 218, user interface 220, illumination light 110, density sensor 120, nephelometric sensor 130, emitter 140, and/or other components of the apparatus 200 such as but not limited to other sensors.

The user interface 220 may be in communication with the processing circuitry 210 to receive an indication of a user input at the user interface 220 and/or to provide an audible, visual, mechanical, or other output to the user. As such, the user interface 220 may include, for example, a keypad, display, a touch screen display and/or other input/output mechanisms. As such, the user interface 220 may, in some example embodiments, provide means for user control of managing or processing data access operations and/or the like. In some example embodiments a user interface 220 may not be present in the detection device, but the user interface may be implemented on a remote device (e.g., smart phone, tablet, personal computer and/or the like) communicatively connected to the detection such as by Bluetooth™ communication or a local area network, for example.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst components of the apparatus 200, the detection device, and/or remote computing devices. In some examples, the communication interface 218 may include a network configured to transmit information amongst various devices. Accordingly, the communication interface 218 may, for example, include supporting hardware and/or software for enabling wireless and/or wireline communications via cable, digital subscriber line (DSL), universal serial bus (USB), Ethernet, or other methods.

The network in which apparatus 200, the detection device, and/or any of the components thereof may operate may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

With reference to FIG. 9, an example detection device 1 (also referred to as a testing instrument or optical instrument) is shown. In the depicted embodiment, the detection device 1 holds two sample tubes 100 for optical density testing. The detection device 1 may comprise a handheld unit 10 and a base station 20. In some embodiments, the handheld unit is battery operated for convenience and flexibility and includes the optical test platform detailed herein. The handheld unit 10 may transmit data to the base station 20 via Bluetooth® or another wireless or wired protocol that permits real time data transfer. The base station 20 may then be wire or wirelessly connected to a computer for receiving the optical density data in real time. In some embodiments, the handheld unit 10 may hold two sample tubes or a fused, dual sample tube 100. Further details regarding the instrument, its structure, and operation may be found in U.S. Provisional Application No. 62/487,796, entitled "OPTICAL DENSITY INSTRUMENT AND SYSTEMS AND METHODS USING THE SAME," which application is incorporated by reference herein in its entirety.

With reference to FIG. 10, an example shell 910, which is disposed within the handheld unit 10, is shown. The shell 910 may be molded of an opaque or semi-opaque material. In some further embodiments, the shell 910 may be formed of a dark color polymer. In yet some further embodiments, the shell 910 may be formed of a black polymer. The windows 902, 904, 906, 108 allow light to pass through the shell 910 at generally perpendicular angles to the surface of the window, with the shell material prohibiting light from propagating through the shell itself. The shell 910 may define one or more cavities 912a, 912b (collectively "912") therein. The cavities 912 may receive the sample tubes 100 (shown in FIGS. 1 and 9) through an upper aperture 914a, 914b (collectively "914"), and the sample tubes 100 may be supported by the shell. In some embodiments, the cavities 912 may be substantially cylindrical, and in some embodiments, the cavities 912 may be bounded by one or more walls 916a, 916b.

The shell 910 may hold any of several configurations of sample tubes 100. For example, in the depicted embodiment of FIG. 3, the shell 910 includes two cavities 912a, 912b configured to receive two corresponding sample tubes 100. The depicted embodiment is configured to test one of the two tubes (e.g., the optical components only interrogate one of the two cavities, cavity 912a), while the second cavity 912b is left for convenience to hold a second tube. For example, once the optical density of the tube 100 in the first cavity 912a reaches a desired concentration, separate samples based on that concentration may be made in the second tube 100 (e.g., diluted versions of the original concentration based on the known concentration of the tube in the first cavity 912a, such as for antibiotic susceptibility testing). This dual sample tube configuration is useful for use with a dual-test tube or other fused sample tubes, where the two tubes should be kept together for study but need not be independently checked with optical density sensors. In some alternative embodiments, two or more optical components may be used to interrogate the second cavity 912b. Although the description herein refers to interrogating a single sample tube, these teachings may be readily applied to a second set of optical components operating on the second cavity 912b. In some alternative embodiments, the optical test platform may include only a single cavity for testing a single sample tube, or in some embodiments, greater than two sample tubes may be used with one, two, or more sets of optical components for interrogating the respective tubes. The cavities 912 may include a support ring 146 or fillet for engaging and supporting the sample tubes 100.

The shell 910 may include one or more mounts 920, 922, 924 for engaging and supporting the optical components (e.g., the emitter 140, density sensor 120, nephelometric sensor 130, and/or illumination light 110 shown in FIG. 1). In the embodiments shown in FIG. 10, the first mount 920 may receive and engage the emitter 140, the second mount 922 may receive and engage the nephelometric sensor 130, and the third mount 924 may receive and engage the density sensor 120. One of ordinary skill in the art will also appreciate, in light of this disclosure, that the mounts 920, 922, 924 and optical components 110, 120, 130, 140 may be reconfigured to any arrangement that satisfies the possible emitter-sensor relationships discussed herein. In some embodiments, the mounts 920, 922, 924 may be integrally molded with the shell 910, and in some other embodiments, the mounts 920, 922, 924 may be separately attached to the shell.

With continued reference to FIG. 10, an illustration of the optical coupling of the emitters and sensors is shown. In the depicted embodiment of FIG. 10, the emitter 140 (shown in FIG. 1) would be attached to the first mount 920, the density sensor 120 (shown in FIG. 1) would be attached to the third mount 924, and the nephelometric sensor 130 (shown in FIG. 1) would be attached to the second mount 922. In operation, the emitter 140 may emit light 950 into the cavity 912a via window 902. A first portion of the light 952 may be reflected from the sample in the cavity 912a and received by the nephelometric sensor 130, and a second portion of the light 954 may pass through the sample in the cavity 912a and be received by the density sensor 120. In the depicted embodiment, the first window 902, first mount 920, third window 906, and third mount 924 are arranged collinearly (e.g., along axis 30 shown in FIG. 1), and the second window 904 and second mount 922 are perpendicular to the axis of the first window 902, first mount 920, third window 906, and third mount 924 (e.g., on axis 34 shown in FIG. 1). Thus, in the depicted embodiment, the emitter 140 and density sensor 120 would be arranged collinearly, and the nephelometric sensor 130 would be arranged perpendicular to the emitter 140 and first sensor 120.

Although the nephelometric 952 and density 954 signals are shown diverging at the center of the sample, the reflection and dispersion of the emitted light 950 may gradually occur across the length of the cavity 912a assuming an equal distribution of the sample.

Modulating the Illumination Light

In some examples, illumination light 110 may cause interference with detection of a signal by a sensor of the detection device. If the ambient light or supplemental light is too bright, the light may "flood out" or interfere with sensor readings. However, the illumination light 110 may be needed to enable a user to see the tube and tube contents. For example, the density sensor 120 configured to detect source light through the tube 100 and/or the nephelometric sensor 130 configured to detect reflected or scattered source light from particles in the tube may be impacted by the illumination light 110 such that the readings become inaccurate. Example embodiments may therefore modulate the illumination light 110 such that sensor readings may be performed when the illumination light 110 is off. In some embodiments, interference between the illumination light 110 and the emitter 140 signal may be reduced with time-division multiplexing as described herein.

FIG. 3 is a flowchart illustrating example operations of apparatus 200 according to some example embodiments. As shown by operation 300 of FIG. 3, apparatus 200 may include means, such as processing circuitry 210, processor 212, memory 214, communication interface 218, illumination light 110, and/or the like, for causing an illumination light (e.g., illumination light 110) to be powered on and off according to a light modulation pattern having on cycles and off cycles for the illumination light.

FIG. 4 is an example timing diagram of a light modulation pattern according to example embodiments. After tube insertion (400), the illumination light 110 may be powered on (402) and off (404) for a predetermined interval of time. In some embodiments, the light modulation pattern may be configured to begin in response to an indication of a tube insertion. The indication may be provided in response to triggering of a physical switch in the detection device and/or user input to user interface 220, for example. The time intervals of the on and off cycles may be any predetermined or dynamically determined period of time. The time interval of an on cycle may be the same or different as that of an off cycle, and in some example, the intervals may change or vary. The example light modulation pattern of FIG. 4 indicates an 8 millisecond (ms) on cycle followed by an 8 ms off cycle, repeated. In this regard, the illumination light 110 is modulated with a 16 ms period and 50% duty cycle (403).

The light modulation pattern may be determined such that the illumination light 110 is powered on for durations adequate for enabling supplemental light to be provided for the practitioner or user to view the suspension in the tube, but powered off for durations such that the supplemental illumination appears constant to the user. In this regard, no flickering or an insignificant amount of flickering may be apparent to the user such that the illumination light appears constant. Accordingly, awareness of the light modulation pattern by the user, or visibility of the light modulation pattern to the user may be reduced, minimized and/or prevented. The time intervals of the on and/or off cycle may therefore be determined based on a variety of factors including but not limited to the type, size, and/or luminosity of illumination light 110. Other timing intervals than those illustrated may therefore be used. For example, in some embodiments, the illumination light 110 may cycle on and off for intervals of 10 ms.

In some embodiments, the longest off cycle may be defined by the period a human can tolerate the illumination light being off. For example, in some embodiments, the off cycle may be 16.66 ms or less (e.g., 30 Hz cycle or greater). In some embodiments, the shortest off cycle may be defined by the time required to process a sensor reading. For example, in some embodiments and for some sensors, a sensor may require 6 ms to process a reading. In such embodiments, the off cycle may be 6 ms or greater (e.g., 84 Hz cycle or less). In some embodiments and for some sensors, a sensor may require 8 ms to process a reading. In such embodiments, the off cycle may be 8 ms or greater (e.g., 65 Hz cycle or less).

Thus, in some embodiments, the off cycle of the light modulation pattern may be from 6 ms to 16.66 ms. In some embodiments, the off cycle of the light modulation pattern may be from 5 ms to 16.66 ms. In some embodiments, the off cycle of the light modulation pattern may be from 4 ms to 16.66 ms. In some embodiments, the off cycle of the light modulation pattern may be from 3 ms to 16.66 ms. In some embodiments, the off cycle of the light modulation pattern may be from 2 ms to 16.66 ms. In some embodiments, the off cycle of the light modulation pattern may be from 6 ms to 16 ms. In some embodiments, the off cycle of the light modulation pattern may be from 5 ms to 16 ms. In some embodiments, the off cycle of the light modulation pattern may be from 4 ms to 16 ms. In some embodiments, the off cycle of the light modulation pattern may be from 3 ms to 16 ms. In some embodiments, the off cycle of the light modulation pattern may be from 2 ms to 16 ms. In some embodiments, the off cycle of the light modulation pattern may be from 6 ms to 17 ms. In some embodiments, the off cycle of the light modulation pattern may be from 5 ms to 17 ms. In some embodiments, the off cycle of the light modulation pattern may be from 4 ms to 17 ms. In some embodiments, the off cycle of the light modulation pattern may be from 3 ms to 17 ms. In some embodiments, the off cycle of the light modulation pattern may be from 2 ms to 17 ms. In some embodiments, the off cycle of the light modulation pattern may be from 2 ms to 20 ms. In some embodiments, the off cycle of the light modulation pattern may be from 2 ms to 19 ms. In some embodiments, the off cycle of the light modulation pattern may be from 2 ms to 18 ms. In some embodiments, the off cycle of the light modulation pattern may be from 2 ms to 15 ms. In some embodiments, the off cycle of the light modulation pattern may be from 2 ms to 14 ms. In some embodiments, the off cycle of the light modulation pattern may be from 2 ms to 13 ms. In some embodiments, the off cycle of the light modulation pattern may be from 2 ms to 12 ms. In some embodiments, the off cycle of the light modulation pattern may be from 2 ms to 11 ms. In some embodiments, the off cycle of the light modulation pattern may be from 2 ms to 10 ms. In some embodiments, the off cycle of the light modulation pattern may be from 2 ms to 9 ms. In some embodiments, the off cycle of the light modulation pattern may be from 2 ms to 8 ms. In some embodiments, the off cycle of the light modulation pattern may be from 2 ms to 7 ms. In some embodiments, the off cycle of the light modulation pattern may be from 2 ms to 6 ms. In some embodiments, the off cycle of the light modulation pattern may be from 2 ms to 5 ms. In some embodiments, the off cycle of the light modulation pattern may be from 2 ms to 4 ms. In some embodiments, the off cycle of the light modulation pattern may be from 2 ms to 3 ms. In some embodiments, the off cycle of the light modulation pattern may be from 3 ms to 20 ms. In some embodiments, the off cycle of the light modulation pattern may be from 4 ms to 20 ms. In some embodiments, the off cycle of the light modulation pattern may be from 5 ms to 20 ms. In some embodiments, the off cycle of the light modulation pattern may be from 6 ms to 20 ms. In some embodiments, the off cycle of the light modulation pattern may be from 7 ms to 20 ms. In some embodiments, the off cycle of the light modulation pattern may be from 8 ms to 20 ms. In some embodiments, the off cycle of the light modulation pattern may be from 9 ms to 20 ms. In some embodiments, the off cycle of the light modulation pattern may be from 10 ms to 20 ms. In some embodiments, the off cycle of the light modulation pattern may be from 11 ms to 20 ms. In some embodiments, the off cycle of the light modulation pattern may be from 12 ms to 20 ms. In some embodiments, the off cycle of the light modulation pattern may be from 13 ms to 20 ms. In some embodiments, the off cycle of the light modulation pattern may be from 14 ms to 20 ms. In some embodiments, the off cycle of the light modulation pattern may be from 15 ms to 20 ms. In some embodiments, the off cycle of the light modulation pattern may be from 16 ms to 20 ms. In some embodiments, the off cycle of the light modulation pattern may be from 17 ms to 20 ms. In some embodiments, the off cycle of the light modulation pattern may be from 18 ms to 20 ms. In some embodiments, the off cycle of the light modulation pattern may be from 19 ms to 20 ms.

Thus, in some embodiments, the on cycle of the light modulation pattern may be from 6 ms to 16.66 ms. In some embodiments, the on cycle of the light modulation pattern may be from 5 ms to 16.66 ms. In some embodiments, the on cycle of the light modulation pattern may be from 4 ms to 16.66 ms. In some embodiments, the on cycle of the light modulation pattern may be from 3 ms to 16.66 ms. In some embodiments, the on cycle of the light modulation pattern may be from 2 ms to 16.66 ms. In some embodiments, the on cycle of the light modulation pattern may be from 6 ms to 16 ms. In some embodiments, the on cycle of the light modulation pattern may be from 5 ms to 16 ms. In some embodiments, the on cycle of the light modulation pattern may be from 4 ms to 16 ms. In some embodiments, the on cycle of the light modulation pattern may be from 3 ms to 16 ms. In some embodiments, the on cycle of the light modulation pattern may be from 2 ms to 16 ms. In some embodiments, the on cycle of the light modulation pattern may be from 6 ms to 17 ms. In some embodiments, the on cycle of the light modulation pattern may be from 5 ms to 17 ms. In some embodiments, the on cycle of the light modulation pattern may be from 4 ms to 17 ms. In some embodiments, the on cycle of the light modulation pattern may be from 3 ms to 17 ms. In some embodiments, the on cycle of the light modulation pattern may be from 2 ms to 17 ms. In some embodiments, the on cycle of the light modulation pattern may be from 2 ms to 20 ms. In some embodiments, the on cycle of the light modulation pattern may be from 2 ms to 19 ms. In some embodiments, the on cycle of the light modulation pattern may be from 2 ms to 18 ms. In some embodiments, the on cycle of the light modulation pattern may be from 2 ms to 15 ms. In some embodiments, the on cycle of the light modulation pattern may be from 2 ms to 14 ms. In some embodiments, the on cycle of the light modulation pattern may be from 2 ms to 13 ms. In some embodiments, the on cycle of the light modulation pattern may be from 2 ms to 12 ms. In some embodiments, the on cycle of the light modulation pattern may be from 2 ms to 11 ms. In some embodiments, the on cycle of the light modulation pattern may be from 2 ms to 10 ms. In some embodiments, the on cycle of the light modulation pattern may be from 2 ms to 9 ms. In some embodiments, the on cycle of the light modulation pattern may be from 2 ms to 8 ms. In some embodiments, the on cycle of the light modulation pattern may be from 2 ms to 7 ms. In some embodiments, the on cycle of the light modulation pattern may be from 2 ms to 6 ms. In some embodiments, the on cycle of the light modulation pattern may be from 2 ms to 5 ms. In some embodiments, the on cycle of the light modulation pattern may be from 2 ms to 4 ms. In some embodiments, the on cycle of the light modulation pattern may be from 2 ms to 3 ms. In some embodiments, the on cycle of the light modulation pattern may be from 3 ms to 20 ms. In some embodiments, the on cycle of the light modulation pattern may be from 4 ms to 20 ms. In some embodiments, the on cycle of the light modulation pattern may be from 5 ms to 20 ms. In some embodiments, the on cycle of the light modulation pattern may be from 6 ms to 20 ms. In some embodiments, the on cycle of the light modulation pattern may be from 7 ms to 20 ms. In some embodiments, the on cycle of the light modulation pattern may be from 8 ms to 20 ms. In some embodiments, the on cycle of the light modulation pattern may be from 9 ms to 20 ms. In some embodiments, the on cycle of the light modulation pattern may be from 10 ms to 20 ms. In some embodiments, the on cycle of the light modulation pattern may be from 11 ms to 20 ms. In some embodiments, the on cycle of the light modulation pattern may be from 12 ms to 20 ms. In some embodiments, the on cycle of the light modulation pattern may be from 13 ms to 20 ms. In some embodiments, the on cycle of the light modulation pattern may be from 14 ms to 20 ms. In some embodiments, the on cycle of the light modulation pattern may be from 15 ms to 20 ms. In some embodiments, the on cycle of the light modulation pattern may be from 16 ms to 20 ms. In some embodiments, the on cycle of the light modulation pattern may be from 17 ms to 20 ms. In some embodiments, the on cycle of the light modulation pattern may be from 18 ms to 20 ms. In some embodiments, the on cycle of the light modulation pattern may be from 19 ms to 20 ms.

In some embodiments, the off cycle of the light modulation pattern may be less than 21 ms. In some embodiments, the off cycle of the light modulation pattern may be less than 20 ms. In some embodiments, the off cycle of the light modulation pattern may be less than 19 ms. In some embodiments, the off cycle of the light modulation pattern may be less than 18 ms. In some embodiments, the off cycle of the light modulation pattern may be less than 17 ms. In some embodiments, the off cycle of the light modulation pattern may be less than 16 ms. In some embodiments, the off cycle of the light modulation pattern may be less than 15 ms. In some embodiments, the off cycle of the light modulation pattern may be less than 14 ms. In some embodiments, the off cycle of the light modulation pattern may be less than 13 ms. In some embodiments, the off cycle of the light modulation pattern may be less than 12 ms. In some embodiments, the off cycle of the light modulation pattern may be less than 11 ms. In some embodiments, the off cycle of the light modulation pattern may be less than 10 ms. In some embodiments, the off cycle of the light modulation pattern may be less than 9 ms. In some embodiments, the off cycle of the light modulation pattern may be less than 8 ms. In some embodiments, the off cycle of the light modulation pattern may be less than 7 ms. In some embodiments, the off cycle of the light modulation pattern may be less than 6 ms. In some embodiments, the off cycle of the light modulation pattern may be less than 5 ms. In some embodiments, the off cycle of the light modulation pattern may be less than 4 ms. In some embodiments, the off cycle of the light modulation pattern may be less than 3 ms. In some embodiments, the off cycle of the light modulation pattern may be less than 2 ms.

In some embodiments, the on cycle of the light modulation pattern may be less than 21 ms. In some embodiments, the on cycle of the light modulation pattern may be less than 20 ms. In some embodiments, the on cycle of the light modulation pattern may be less than 19 ms. In some embodiments, the on cycle of the light modulation pattern may be less than 18 ms. In some embodiments, the on cycle of the light modulation pattern may be less than 17 ms. In some embodiments, the on cycle of the light modulation pattern may be less than 16 ms. In some embodiments, the on cycle of the light modulation pattern may be less than 15 ms. In some embodiments, the on cycle of the light modulation pattern may be less than 14 ms. In some embodiments, the on cycle of the light modulation pattern may be less than 13 ms. In some embodiments, the on cycle of the light modulation pattern may be less than 12 ms. In some embodiments, the on cycle of the light modulation pattern may be less than 11 ms. In some embodiments, the on cycle of the light modulation pattern may be less than 10 ms. In some embodiments, the on cycle of the light modulation pattern may be less than 9 ms. In some embodiments, the on cycle of the light modulation pattern may be less than 8 ms. In some embodiments, the on cycle of the light modulation pattern may be less than 7 ms. In some embodiments, the on cycle of the light modulation pattern may be less than 6 ms. In some embodiments, the on cycle of the light modulation pattern may be less than 5 ms. In some embodiments, the on cycle of the light modulation pattern may be less than 4 ms. In some embodiments, the on cycle of the light modulation pattern may be less than 3 ms. In some embodiments, the on cycle of the light modulation pattern may be less than 2 ms.

In some embodiments, as described herein, the on cycle and off cycle of the light modulation pattern may have the same duration, which may include any pair of ranges or durations noted herein (e.g., 2 ms on, 2 ms off; 3 ms on, 3 ms off; 4 ms on, 4 ms off; 5 ms on, 5 ms off; 6 ms on, 6 ms off; 7 ms on, 7 ms off; 8 ms on, 8 ms off; 9 ms on, 9 ms off; 10 ms on, 10 ms off; 11 ms on, 11 ms off; 12 ms on, 12 ms off; 13 ms on, 13 ms off; 14 ms on, 14 ms off; 15 ms on, 15 ms off; 16 ms on, 16 ms off; 17 ms on, 17 ms off; 18 ms on, 18 ms off; 19 ms on, 19 ms off; 20 ms on, 20 ms off; etc.). In some embodiments, the on cycle and off cycle may have different durations in accordance with any of the ranges or durations noted herein. In some embodiments, the on cycle of the light modulation pattern may be longer than the off cycle of the light modulation pattern. In some embodiments, the off cycle of the light modulation pattern may be longer than the on cycle of the light modulation pattern.

As shown by operation 302 of FIG. 3, apparatus 200 may include means, such as processing circuitry 210, processor 212, memory 214, communication interface 218, emitter 140, and/or the like, for controlling at least one sensor to perform a dark reading while the at least one emitter (e.g., emitter 140) is off.

In some examples, the apparatus 200 may be configured to control the sensors such that sensor readings begin after a predetermined time delay following tube insertion. For example, as indicated in FIG. 4, a delay (410) of 500 ms or other predetermined time may occur from the time of tube insertion to the start of sensor readings to account for the time needed for a user to insert the tube into the detection device after the apparatus detects the tube being inserted (e.g., using a physical, optical, or other type of switch).

A sensor reading may begin (412) and end (414) within a single off cycle of the illumination light 110. Once the sensor readings begin (412), sensor readings may be repeated on a continuous cycle, such as every 192 ms (416) until the tube is removed (420). The repeated sensor readings are described in further detail below with respect to operations 312 and 314.

In some embodiments, the sensor readings may be taken every off cycle of the illumination light 110 (e.g., an interval corresponding to any of the intervals of the off cycle of the light modulation pattern detailed herein). In some embodiments, the sensor readings may be taken after a predetermined number of off cycles of the illumination light. Said differently, the interval between readings (416) may be a multiple of the duty cycle 403 and off cycle duration 404. For example, in the embodiment depicted in FIG. 4, the interval between readings is 192 ms (416), which is a multiple (12×) of the 16 ms duty cycle (403).

In some embodiments, the interval between readings (416) may be less than 2 times the length of the duty cycle (403). In some embodiments, the interval between readings (416) may be less than 3 times the length of the duty cycle (403). In some embodiments, the interval between readings (416) may be less than 4 times the length of the duty cycle (403). In some embodiments, the interval between readings (416) may be less than 5 times the length of the duty cycle (403). In some embodiments, the interval between readings (416) may be less than 6 times the length of the duty cycle (403). In some embodiments, the interval between readings (416) may be less than 7 times the length of the duty cycle (403). In some embodiments, the interval between readings (416) may be less than 8 times the length of the duty cycle (403). In some embodiments, the interval between readings (416) may be less than 9 times the length of the duty cycle (403). In some embodiments, the interval between readings (416) may be less than 10 times the length of the duty cycle (403). In some embodiments, the interval between readings (416) may be less than 11 times the length of the duty cycle (403). In some embodiments, the interval between readings (416) may be less than 12 times the length of the duty cycle (403). In some embodiments, the interval between readings (416) may be less than 13 times the length of the duty cycle (403). In some embodiments, the interval between readings (416) may be less than 14 times the length of the duty cycle (403). In some embodiments, the interval between readings (416) may be less than 15 times the length of the duty cycle (403). In some embodiments, the interval between readings (416) may be less than 16 times the length of the duty cycle (403). In some embodiments, the interval between readings (416) may be less than 17 times the length of the duty cycle (403). In some embodiments, the interval between readings (416) may be less than 18 times the length of the duty cycle (403). In some embodiments, the interval between readings (416) may be less than 19 times the length of the duty cycle (403). In some embodiments, the interval between readings (416) may be less than 20 times the length of the duty cycle (403). In some embodiments, the interval between readings (416) may be less than 21 times the length of the duty cycle (403).

In some embodiments, the interval between readings (416) may be less than 500 ms. In some embodiments, the interval between readings (416) may be less than 300 ms. In some embodiments, the interval between readings (416) may be less than 450 ms. In some embodiments, the interval between readings (416) may be less than 400 ms. In some embodiments, the interval between readings (416) may be less than 350 ms. In some embodiments, the interval between readings (416) may be less than 300 ms. In some embodiments, the interval between readings (416) may be less than 250 ms. In some embodiments, the interval between readings (416) may be less than 200 ms. In some embodiments, the interval between readings (416) may be less than 150 ms. In some embodiments, the interval between readings (416) may be less than 100 ms. In some embodiments, the interval between readings (416) may be less than 50 ms.

In some embodiments, the interval between readings (416) may be 320 ms or less. In some embodiments, the interval between readings (416) may be 304 ms or less. In some embodiments, the interval between readings (416) may be 288 ms or less. In some embodiments, the interval between readings (416) may be 272 ms or less. In some embodiments, the interval between readings (416) may be 256 ms or less. In some embodiments, the interval between readings (416) may be 240 ms or less. In some embodiments, the interval between readings (416) may be 224 ms or less. In some embodiments, the interval between readings (416) may be 208 ms or less. In some embodiments, the interval between readings (416) may be 192 ms or less. In some embodiments, the interval between readings (416) may be 176 ms or less. In some embodiments, the interval between readings (416) may be 160 ms or less. In some embodiments, the interval between readings (416) may be 144 ms or less. In some embodiments, the interval between readings (416) may be 128 ms or less. In some embodiments, the interval between readings (416) may be 112 ms or less. In some embodiments, the interval between readings (416) may be 96 ms or less. In some embodiments, the interval between readings (416) may be 80 ms or less. In some embodiments, the interval between readings (416) may be 64 ms or less. In some embodiments, the interval between readings (416) may be 48 ms or less. In some embodiments, the interval between readings (416) may be 32 ms or less. In some embodiments, the interval between readings (416) may be 16 ms or less.

In some embodiments, the interval between readings (416) may be from 1 to 20 times the length of the duty cycle (403). In some embodiments, the interval between readings (416) may be from 2 to 20 times the length of the duty cycle (403). In some embodiments, the interval between readings (416) may be from 4 to 20 times the length of the duty cycle (403). In some embodiments, the interval between readings (416) may be from 6 to 20 times the length of the duty cycle (403). In some embodiments, the interval between readings (416) may be from 8 to 20 times the length of the duty cycle (403). In some embodiments, the interval between readings (416) may be from 10 to 20 times the length of the duty cycle (403). In some embodiments, the interval between readings (416) may be from 12 to 20 times the length of the duty cycle (403). In some embodiments, the interval between readings (416) may be from 14 to 20 times the length of the duty cycle (403). In some embodiments, the interval between readings (416) may be from 16 to 20 times the length of the duty cycle (403). In some embodiments, the interval between readings (416) may be from 18 to 20 times the length of the duty cycle (403). In some embodiments, the interval between readings (416) may be from 1 to 18 times the length of the duty cycle (403). In some embodiments, the interval between readings (416) may be from 1 to 16 times the length of the duty cycle (403). In some embodiments, the interval between readings (416) may be from 1 to 14 times the length of the duty cycle (403). In some embodiments, the interval between readings (416) may be from 1 to 12 times the length of the duty cycle (403). In some embodiments, the interval between readings (416) may be from 1 to 10 times the length of the duty cycle (403). In some embodiments, the interval between readings (416) may be from 1 to 8 times the length of the duty cycle (403). In some embodiments, the interval between readings (416) may be from 1 to 6 times the length of the duty cycle (403). In some embodiments, the interval between readings (416) may be from 1 to 4 times the length of the duty cycle (403). In some embodiments, the interval between readings (416) may be from 1 to 2 times the length of the duty cycle (403). In some embodiments, the interval between readings (416) may be from 6 to 18 times the length of the duty cycle (403). In some embodiments, the interval between readings (416) may be from 8 to 18 times the length of the duty cycle (403). In some embodiments, the interval between readings (416) may be from 10 to 18 times the length of the duty cycle (403). In some embodiments, the interval between readings (416) may be from 12 to 18 times the length of the duty cycle (403). In some embodiments, the interval between readings (416) may be from 14 to 18 times the length of the duty cycle (403). In some embodiments, the interval between readings (416) may be from 6 to 16 times the length of the duty cycle (403). In some embodiments, the interval between readings (416) may be from 6 to 14 times the length of the duty cycle (403). In some embodiments, the interval between readings (416) may be from 6 to 12 times the length of the duty cycle (403). In some embodiments, the interval between readings (416) may be from 6 to 10 times the length of the duty cycle (403). In some embodiments, the interval between readings (416) may be from 6 to 8 times the length of the duty cycle (403).

In some embodiments, the interval between readings (416) may be from 100 ms to 500 ms. In some embodiments, the interval between readings (416) may be from 150 ms to 500 ms. In some embodiments, the interval between readings (416) may be from 200 ms to 500 ms. In some embodiments, the interval between readings (416) may be from 250 ms to 500 ms. In some embodiments, the interval between readings (416) may be from 300 ms to 500 ms. In some embodiments, the interval between readings (416) may be from 350 ms to 500 ms. In some embodiments, the interval between readings (416) may be from 400 ms to 500 ms. In some embodiments, the interval between readings (416) may be from 450 ms to 500 ms. In some embodiments, the interval between readings (416) may be from 100 ms to 450 ms. In some embodiments, the interval between readings (416) may be from 100 ms to 400 ms. In some embodiments, the interval between readings (416) may be from 100 ms to 350 ms. In some embodiments, the interval between readings (416) may be from 100 ms to 300 ms. In some embodiments, the interval between readings (416) may be from 100 ms to 250 ms. In some embodiments, the interval between readings (416) may be from 100 ms to 200 ms. In some embodiments, the interval between readings (416) may be from 100 ms to 150 ms. In some embodiments, the interval between readings (416) may be from 192 ms to 256 ms. In some embodiments, the interval between readings (416) may be from 192 ms to 240 ms. In some embodiments, the interval between readings (416) may be from 192 ms to 224 ms. In some embodiments, the interval between readings (416) may be from 192 ms to 208 ms. In some embodiments, the interval between readings (416) may be from 176 ms to 192 ms. In some embodiments, the interval between readings (416) may be from 160 ms to 192 ms. In some embodiments, the interval between readings (416) may be from 144 ms to 192 ms. In some embodiments, the interval between readings (416) may be from 128 ms to 192 ms. In some embodiments, the interval between readings (416) may be from 176 ms to 256 ms. In some embodiments, the interval between readings (416) may be from 176 ms to 240 ms. In some embodiments, the interval between readings (416) may be from 176 ms to 224 ms. In some embodiments, the interval between readings (416) may be from 176 ms to 208 ms. In some embodiments, the interval between readings (416) may be from 176 ms to 192 ms. In some embodiments, the interval between readings (416) may be from 160 ms to 176 ms. In some embodiments, the interval between readings (416) may be from 144 ms to 176 ms. In some embodiments, the interval between readings (416) may be from 128 ms to 176 ms. In some embodiments, the interval between readings (416) may be from 144 ms to 256 ms. In some embodiments, the interval between readings (416) may be from 144 ms to 240 ms. In some embodiments, the interval between readings (416) may be from 144 ms to 224 ms. In some embodiments, the interval between readings (416) may be from 144 ms to 208 ms. In some embodiments, the interval between readings (416) may be from 144 ms to 192 ms. In some embodiments, the interval between readings (416) may be from 144 ms to 176 ms. In some embodiments, the interval between readings (416) may be from 144 ms to 160 ms. In some embodiments, the interval between readings (416) may be from 128 ms to 144 ms. In some embodiments, the interval between readings (416) may be from 128 ms to 256 ms. In some embodiments, the interval between readings (416) may be from 128 ms to 240 ms. In some embodiments, the interval between readings (416) may be from 128 ms to 224 ms. In some embodiments, the interval between readings (416) may be from 128 ms to 208 ms. In some embodiments, the interval between readings (416) may be from 128 ms to 192 ms. In some embodiments, the interval between readings (416) may be from 128 ms to 176 ms. In some embodiments, the interval between readings (416) may be from 128 ms to 160 ms. In some embodiments, the interval between readings (416) may be from 208 ms to 256 ms. In some embodiments, the interval between readings (416) may be from 208 ms to 240 ms. In some embodiments, the interval between readings (416) may be from 208 ms to 224 ms. In some embodiments, the interval between readings (416) may be from 192 ms to 208 ms. In some embodiments, the interval between readings (416) may be from 176 ms to 208 ms. In some embodiments, the interval between readings (416) may be from 160 ms to 208 ms. In some embodiments, the interval between readings (416) may be from 144 ms to 208 ms. In some embodiments, the interval between readings (416) may be from 128 ms to 208 ms. In some embodiments, the interval between readings (416) may be from 224 ms to 256 ms. In some embodiments, the interval between readings (416) may be from 224 ms to 240 ms. In some embodiments, the interval between readings (416) may be from 208 ms to 224 ms. In some embodiments, the interval between readings (416) may be from 192 ms to 224 ms. In some embodiments, the interval between readings (416) may be from 176 ms to 224 ms. In some embodiments, the interval between readings (416) may be from 160 ms to 224 ms. In some embodiments, the interval between readings (416) may be from 144 ms to 224 ms. In some embodiments, the interval between readings (416) may be from 128 ms to 224 ms. In some embodiments, the interval between readings (416) may be from 240 ms to 256 ms. In some embodiments, the interval between readings (416) may be from 224 ms to 240 ms. In some embodiments, the interval between readings (416) may be from 208 ms to 240 ms. In some embodiments, the interval between readings (416) may be from 192 ms to 240 ms. In some embodiments, the interval between readings (416) may be from 176 ms to 240 ms. In some embodiments, the interval between readings (416) may be from 160 ms to 240 ms. In some embodiments, the interval between readings (416) may be from 144 ms to 240 ms. In some embodiments, the interval between readings (416) may be from 128 ms to 240 ms. In some embodiments, the interval between readings (416) may be from 224 ms to 256 ms. In some embodiments, the interval between readings (416) may be from 208 ms to 256 ms. In some embodiments, the interval between readings (416) may be from 192 ms to 256 ms. In some embodiments, the interval between readings (416) may be from 176 ms to 256 ms. In some embodiments, the interval between readings (416) may be from 160 ms to 256 ms. In some embodiments, the interval between readings (416) may be from 144 ms to 256 ms. In some embodiments, the interval between readings (416) may be from 128 ms to 256 ms.

FIG. 5 is an exploded view of an 8 ms off cycle (500) of the illumination light 110. In some examples, apparatus may control the emitter 140 and/or sensors such that sensor readings are performed following a predetermined time delay (510) following turnoff of the illumination light 110 (520). For example, the apparatus 200 may control the emitter 140 to emit a signal after 2 ms following the end of an on cycle of the light modulation pattern. In this regard, electrons may settle and the ambient light in the vicinity of the tube may stabilize, thereby reducing, minimizing, and/or preventing interference of the illumination light 110 with any of the sensors.

Indicator 530 represents a dark reading(s) performed by a sensor. For example, "D" and "N" of readings 530 represent readings respectively performed by density sensor 120 and nephelometric sensor 130. The term "dark" in dark reading refers to the off status of the emitter 140 and the term dark reading is therefore not intended to be limiting. In some embodiments, the dark reading is used for calibrating any of the sensors to account for ambient light, as described in further detail below. In some embodiments, the dark readings 530 may be less than 1 ms combined. In some embodiments, the dark readings 530 may be 800 microseconds combined. In some embodiments, the dark readings 530 may be 800 microseconds or less combined. In some embodiments, the dark reading time may include an analog to digital conversion (ADC) time and a firmware (FW) execution time.

As described with respect to operation 304, and as shown by indicator 540 in FIG. 5, the apparatus 200 may include means, such as processing circuitry 210, processor 212, memory 214, communication interface 218, emitter 140, and/or the like, for during an off cycle of the light modulation pattern, controlling at least one emitter to emit a signal (e.g., source light) for detection by at least one sensor.

At operation 306, the apparatus 200 may include means, such as processing circuitry 210, processor 212, memory 214, communication interface 218, density sensor 120, nephelometric sensor 130, any other sensor of the detection device, and/or the like, for controlling the at least one sensor to perform a light reading during the off cycle of the light modulation pattern and while the at least one emitter is on.

In this regard, following an optional predetermined time delay (550), the apparatus 200 may direct the sensors to perform a light reading 560. The optional predetermined time delay, such as 4 ms, may be variable, and may be configured to allow the signal or source light emitted from the emitter 540 to be detected by a sensor. Readings "D" and "N" of readings 560 represent light readings respectively performed by density sensor 120 and nephelometric sensor 130. The term "light" in light reading refers to the on or emitting status of the emitter 540 and is not intended to be limiting. For instance, it will be appreciated that the illumination light 110 may indeed be off during a light reading, as is illustrated in FIG. 5. In some embodiments, the light readings 560 may be less than 1 ms combined. In some embodiments, the light readings 560 may be 800 microseconds combined. In some embodiments, the light readings 560 may be 800 microseconds or less combined. In some embodiments, the light reading time may include an analog to digital conversion (ADC) time and a firmware (FW) execution time.

At operation 308, the apparatus 200 may include means, such as processing circuitry 210, processor 212, memory 214, communication interface 218, and/or the like, for determining an ambient light offset by subtracting a dark reading from a light reading. In this regard, the converted and/or digitized readings from the sensors may be used to calculate a quantifiable ambient light offset.

At operation 310, the apparatus 200 may include means, such as processing circuitry 210, processor 212, memory 214, communication interface 218, and/or the like, for calibrating sensor readings according to the ambient light offset. In this regard, the ambient light detected by comparing the dark reading to a light reading may be used to adjust subsequent readings such that the sensor readings account for ambient light. The ambient light offset may be a coefficient or other factor that when applied to a reading performed by a sensor, the adjusted or calibrated reading may account for ambient light such that sensor readings may be more uniformly and/or accurately provided despite ambient light conditions. In this regard, a dark reading and/or calculation of the ambient light offset may occur once following tube insertion or may be repeated any number of times during repeated cycle readings (for example, for each light reading, or for every predetermined number of light readings).

At operation 312, the apparatus 200 may include means, such as processing circuitry 210, processor 212, memory 214, communication interface 218, density sensor 120, nephelometric sensor 130, any other sensor of the detection device, and/or the like, for controlling the at least one sensor to perform a plurality of readings (e.g., light readings) over a plurality of off cycles in the light modulation pattern. The sensor readings may be repeated on a predetermined time interval, such as 192 ms or any other interval discussed herein. Additionally or alternatively, a sensor repeating may be repeated based on an elapsed number of on-off cycles of the illumination light 110 (e.g., 12 cycles). In some embodiments, the apparatus 200 may cause a sensor reading to occur after the time interval (e.g., 192 ms) has elapsed and the illumination light 110 has cycled off, as illustrated in FIGS. 4 (416 and 418).

At operation 314, the apparatus 200 may include means, such as processing circuitry 210, processor 212, memory 214, communication interface 218, and/or the like, for calculating a moving average sensor reading based on the plurality of readings. Example embodiments, may, for example, use a predetermined number of previous readings to calculate a moving average to provide to a user via a user interface or to another device. For example, three previous readings may be used as the predetermined number of readings to incorporate into a moving average. The moving average may serve as a smoothing mechanism for providing readings to another device and/or to a user via a user interface, for example.

In some examples, apparatus 200 may utilize sensor readings from various sensors and/or sensor types, process the sensor readings to calculate a property of a suspension, and provide a moving average. For example, as described in further detail below, apparatus 200 may use a reading from both a density sensor 120 and a nephelometric sensor 130 to determine a McFarland value. In this regard, a reading from both the density sensor 120 and nephelometric sensor 130 may be combined and manipulated to determine a McFarland value, and the readings may be repeated according to configurations of the apparatus 200, and may be represented as a moving average over time. Additionally or alternatively, example embodiments may calculate a moving average based on sensor readings taken from a single sensor.

The 192 ms period on which to repeat sensor readings, and the three-point moving average are provided merely as examples and it will be appreciated that any pattern of sensor readings and moving averages may be used. For example, a 192 ms period and three-point moving average may be determined as appropriate parameters by which to collect data from the density sensor 120 and/or nephelometric sensor 130 and provide resultant data to a user or other computing device based on desired user experience and/or variability in the reported data. However, in some embodiments, apparatus 200 may determine other periods on which to repeat readings and/or other numbers of samples to be used in a moving average depending on a variety of factors such as sensor type, sensor sensitivity, estimated variability in a measured characteristic of the suspension, and/or desired variability in resultant data.

The operations described herein may therefore reduce the interference of the illumination light in sensor readings, and may therefore improve the accuracy of the sensor readings, while still providing improved visibility of liquid in the tube.

Determining McFarland Values from Density Sensor and Nephelometric Sensor Readings In some embodiments, apparatus 200 may advantageously utilize readings from both the density sensor 120 and nephelometric sensor 130 in determining a McFarland value. McFarland values may be used as a reference to adjust turbidity in a suspension so that the concentration of microorganisms may be a specified value or within a range of values to standardize testing.

FIG. 6 is a flowchart illustrating example operations of apparatus 200 according to some example embodiments. In operation 600, the apparatus 200 may include means, such as processing circuitry 210, processor 212, memory 214, communication interface 218, density sensor 120, and/or the like, for receiving a plurality of density sensor readings. In operation 602, the apparatus 200 may include means, such as processing circuitry 210, processor 212, memory 214, communication interface 218, nephelometric sensor 130, and/or the like, for receiving a plurality of nephelometric sensor readings.

FIG. 7 is an example plot of density sensor readings 700 and nephelometric sensor readings 702 according to example embodiments. The readings are plotted as voltages relative to the turbidity of the liquid, and may be non-linear.

In some embodiments, as turbidity increases, nephelometric readings increase, and density readings decrease. In some examples, a density sensor reading may be more sensitive for lower turbidity liquids relative to the sensitivity of the nephelometric readings, whereas nephelometric readings may be more sensitive for higher turbidity liquids relative to the sensitivity of density readings. A polynomial equation may therefore account for the varying impact of the two types of data on the McFarland value.

In some embodiments, apparatus 200 may determine a polynomial equation or model by applying linear regression to the two readings, the output of which provides a McFarland value of the liquid. Said differently, apparatus 200 may calibrate the two signals to generate a McFarland value. In some embodiments, this calibration may be conducted using known samples across a wide range of McFarland values.

Accordingly, in operation 604, the apparatus 200 may include means, such as processing circuitry 210, processor 212, memory 214, communication interface 218, and/or the like, for applying linear regression to the density sensor readings and the nephelometric sensor readings to determine coefficients of a polynomial equation. And, in operation 604, the apparatus 200 may include means, such as processing circuitry 210, processor 212, memory 214, communication interface 218, and/or the like, for applying subsequent readings to the polynomial equation to calculate a McFarland value.

In some embodiments, in operation 608, the apparatus 200 may include means, such as processing circuitry 210, processor 212, memory 214, communication interface 218, and/or the like, for detecting an error in at least one sensor based on a comparison of the density sensor readings and the nephelometric sensor readings. Given previous density sensor readings and/or nephelometric sensor readings, apparatus 200 may be configured to detect a change in one of the sensor readings relative to the other and/or based on the determined polynomial equation. For example, an abnormal reading(s) from one sensor relative to readings of the other sensor, in comparison to a pattern of past density sensor readings and/or nephelometric sensor readings relative to each other may indicate a dirty sensor or window positioned in between a sensor and tube.

In some embodiments, in response to detecting an error, the apparatus 200 may be further configured to calculate a McFarland value based on a correctly functioning sensor(s) not subject to the detected error. Said differently, example embodiments may exclude sensor readings detected from a sensor for which an error is detected. The apparatus 200 may therefore continue to provide McFarland values and/or alert a user to clean device components and/or to troubleshoot the issue.

Zeroing the Detection Device

In some embodiments, apparatus 200 may be configured to zero the detection device and/or a sensor thereof based on an insertion of an empty tube and/or a tube comprising saline or other solution intended to produce a 0 or insignificant sensor reading (e.g., density sensor reading) or calculation (e.g., McFarland value). For simplicity, such a tube may be referred to herein as a baseline tube. The apparatus 200 may then calibrate a sensor(s) and emitter 140 as described below.

FIG. 8 is a flowchart illustrating example operations of apparatus 200 according to some example embodiments. In operation 800, the apparatus 200 may include means, such as processing circuitry 210, processor 212, memory 214, communication interface 218, user interface 220, and/or the like, for receiving an indication to perform a zeroing calibration. A user may insert a baseline tube into the detection device, and indicate via user interface 220 to zero the detection device. As another example, the indication may be generated in response to detection of a baseline tube being inserted into the detection device.

In operation 802, the apparatus 200 may include means, such as processing circuitry 210, processor 212, memory 214, communication interface 218, emitter 140, and/or the like, for in response to the indication of the zeroing calibration, controlling an emitter (e.g., emitter 140) to adjust an emitted signal. For example, when emitter 140 is embodied as an LED, apparatus 200 may cause the current to be gradually stepped up. The LED may be driven by a digital-to-analog converter, such as a 12-bit converter configured to enable the LED to emit 4,096 different levels of current.

As the emitter 140 is gradually stepped up, sensor readings may be performed based on the various signals. In this regard, at operation 804, the apparatus 200 may include means, such as processing circuitry 210, processor 212, memory 214, communication interface 218, density sensor 120, nephelometric sensor 130, any other type sensors and/or the like, for controlling at least one sensor to perform readings based on the emitted signal.

In operation 806, the apparatus 200 may include means, such as processing circuitry 210, processor 212, memory 214, communication interface 218, emitter 140, and/or the like, for monitoring the sensor readings and storing a level of the emitted signal when the sensor reading satisfies a predetermined criterion. The predetermined criterion may be a predetermined target value or range of values the sensor is expected to detect based on an empty tube and/or clear saline solution. As another example, the predetermined criterion may be predetermined target value or range of values of a calculation performed based on a sensor reading, such as a McFarland value calculated based on a density sensor reading and/or nephelometric sensor reading. For example, apparatus 200 may be pre-configured with an expected value or range of values for the density sensor 120 (and/or other types of sensors). Once the target value or range is reached, the level of current emitted by the emitter 140 may be recorded. The calibration may further allow the transmitted signal to normalize by tracking the sensor reading for a period of time and waiting until there is no drift. The normalization may occur before, during, or after the step up of the emitter current, or may be conducted separately therefrom.

In operation 808, the apparatus 200 may include means, such as processing circuitry 210, processor 212, memory 214, communication interface 218, emitter 140, and/or the like, for controlling the emitter to operate based on the stored level of the emitted signal. In this regard, the apparatus 200 may use the calibration (e.g., stored level of emitted signal or current) until the next zeroing calibration occurs. A user may re-zero the detection device when the detection device is turned on, when beginning to use a different type of tube, and/or when ambient conditions change.

Example embodiments therefore provide for more accurate readings by sensors based on ambient conditions, characteristics of the tubes or saline solutions, particular sensor calibrations (e.g., factory calibrations), and/or the like.

Conclusion

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 3, 6 and 8 illustrate operations of a method, apparatus, and computer program product according to some example embodiments. It will be understood that each operation of the flowcharts or diagrams, and combinations of operations in the flowcharts or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. An apparatus for reducing light interference during testing contents of a sample tube, the apparatus comprising:
   a shell defining one or more cavities for receiving at least a portion of a sample tube;
   an illumination light for illuminating the sample tube with visible light for a plurality of illumination light activation periods;
   an emitter configured to emit a source light towards the sample tube; and
   one or more sensors configured to receive at least a portion of the emitted source light during a plurality of sensor reading periods,
   wherein the plurality of illumination light activation periods and the plurality of sensor reading periods are configured to be sequenced such that, for at least a period of time, the illumination light and the one or more sensors appear to be simultaneously illuminating the sample tube and receiving at least a portion of the emitted source light, respectively, while the plurality of illumination light activation periods and the plurality of sensor reading periods do not overlap.

2. The apparatus of claim 1, wherein a first sensor reading period of the plurality of sensor reading periods is initiated based at least in part on receipt of the sample tube in a cavity of the one or more cavities of the shell.

3. The apparatus of claim 2, wherein the cavity comprises a physical switch that is triggered by the sample tube in the cavity thereby indicating insertion of the sample tube in the cavity.

4. The apparatus of claim 2, wherein the apparatus further comprises a user interface and the receipt of the sample tube in the cavity is based on user input to the user interface indicating insertion of the sample tube in the cavity.

5. The apparatus of claim 1, wherein the plurality of illumination light activation periods are alternated in time with a plurality of illumination light inactivation periods.

6. The apparatus of claim 5, wherein each of the plurality of illumination light inactivation periods defines a duration less than 21 ms.

7. The apparatus of claim 1, wherein the illumination light is configured to allow at least a portion of contents of the sample tube to be observable by a user outside the apparatus during a testing of the contents.

8. A method for operating an optical testing instrument to reduce light interference from an illumination light in sensor readings, the method comprising:
   receiving an indication of a sample tube insertion;

causing an illumination light to illuminate the inserted sample tube with visible light during each of a plurality of illumination light activation periods;

controlling an emitter to emit a signal towards the sample tube for detection by one or more sensors; and receiving at least a portion of the emitted source light with the one or more sensors during a plurality of sensor reading periods, wherein a first sensor reading period of the plurality of sensor reading periods is based at least in part on the receipt of the indication of the sample tube insertion, wherein the plurality of illumination light activation periods and the plurality of sensor reading periods are configured to be sequenced such that, for at least a period of time, the illumination light and the one or more sensors appear to be simultaneously illuminating the sample tube and receiving at least a portion of the emitted source light, respectively, while the plurality of illumination light activation periods and the plurality of sensor reading periods do not overlap.

9. The method of claim 8, wherein the first sensor reading period of the plurality of sensor reading periods begins following completion of a predetermined initial delay after the receipt of the indication of the sample tube insertion.

10. The method of claim 8, wherein the indication of the sample tube insertion is based on a triggering of a physical switch.

11. The method of claim 8, wherein the plurality of illumination light activation periods are alternated in time with a plurality of illumination light inactivation periods.

12. The method of claim 11, wherein the method further comprises:

during at least one illumination light inactivation period of the plurality of illumination light inactivation periods, controlling the emitter to emit a signal during an emitter activation period, wherein the emitter activation period begins following completion of a predetermined emitter time delay, the predetermined emitter time delay triggered by expiration of the illumination light activation period immediately preceding in time the at least one illumination light inactivation period.

13. The method of claim 12, wherein the method further comprises:

controlling at least one sensor of the one or more sensors to perform a first sensor reading following completion of a predetermined sensor time delay, the predetermined sensor time delay triggered by expiration of the illumination light activation period.

14. The method of claim 13, wherein the predetermined sensor time delay is less than the predetermined emitter time delay such that the first sensor reading is a dark reading performed during the predetermined emitter time delay and the at least one illumination light inactivation period.

15. The method of claim 14, wherein the method further comprises:

controlling the at least one sensor of the one or more sensors to perform a second sensor reading, wherein the second sensor reading is performed during the emitter activation period such that the second sensor reading is a light reading.

16. The method of claim 15, wherein the method further comprises:

determining an ambient light offset value for the at least one sensor, the ambient light offset value of the at least one sensor based on subtracting the first sensor reading from the second sensor reading; and calibrating subsequent sensor readings of the at least one sensor according to the ambient light offset value.

17. The method of claim 8, wherein the illumination light is configured to allow at least a portion of contents of the inserted sample tube to be observable by a user outside the optical testing instrument during a testing of the contents.

18. The method of claim 8, wherein the one or more sensors comprise at least one density sensor and at least one nephelometric sensor, the method further comprising:

detecting a sensor error in at least one sensor of the one or more sensors based on a comparison of density sensor readings and nephelometric sensor readings.

19. The method of claim 18, wherein detecting the sensor error in at least one sensor of the one or more sensors comprises:

detecting at least one variation or abnormal sensor reading performed by a first sensor relative to sensor readings performed by a second sensor in comparison to a pattern of past density sensor readings, past nephelometric sensor readings, or combination of past density sensor readings and past nephelometric sensor readings relative to each other.

20. An apparatus for reducing light interference during testing contents of a sample tube, the apparatus comprising:

means for receiving at least a portion of a sample tube;

means for illuminating the sample tube with visible light for a plurality of illumination periods;

means for emitting a source light towards the sample tube; and means for receiving at least a portion of the emitted source light during a plurality of reading periods, wherein the plurality of illumination periods and the plurality of reading periods are configured to be sequenced such that, for at least a period of time, the means for illuminating the sample tube with visible light and the means for receiving at least a portion of the emitted source light appear to be simultaneously illuminating the sample tube and receiving at least a portion of the emitted source light, respectively, while the plurality of illumination periods and the plurality of reading periods do not overlap.

* * * * *